United States Patent [19]
Taniguchi et al.

[11] Patent Number: 6,025,375
[45] Date of Patent: Feb. 15, 2000

[54] 4,5-DIARYLOXAZOLE DERIVATIVES

[75] Inventors: Kiyoshi Taniguchi, Kobe; Masanobu Nagano, Kagoshima; Kouji Hattori, Takarazuka; Kazunori Tsubaki, Uji; Osamu Okitsu; Seiichiro Tabuchi, both of Nishinomiya, all of Japan

[73] Assignee: Fujisawa Pharmaceutical Co., Ltd., Osaka, Japan

[21] Appl. No.: 09/092,027

[22] Filed: Jun. 5, 1998

Related U.S. Application Data

[63] Continuation of application No. 08/646,261, filed as application No. PCT/JP94/02116, Dec. 16, 1994, abandoned.

[30] Foreign Application Priority Data

Dec. 20, 1993 [GB] United Kingdom ............... 9325962
Nov. 7, 1994 [GB] United Kingdom ............... 9422404

[51] Int. Cl.$^7$ .................. A01K 31/42; C07D 263/34
[52] U.S. Cl. ............................. 514/374; 548/236
[58] Field of Search ............... 514/374; 548/236

[56] References Cited

U.S. PATENT DOCUMENTS

| | | | |
|---|---|---|---|
| 3,578,671 | 5/1971 | Brown ........................ | 514/374 |
| 4,072,689 | 2/1978 | Tarzia ........................ | 548/236 |
| 5,348,969 | 9/1994 | Romine et al. ............. | 514/374 |
| 5,763,489 | 6/1998 | Taniguchi et al. .......... | 514/551 |

FOREIGN PATENT DOCUMENTS 0 434 034  6/1991  European Pat. Off. .

OTHER PUBLICATIONS

Meanwell et al. J. Med Chem vol. 35, pp. 3483–3497, (1992).
Meanwell et al Chem. ABSTR vol. 117 p. 820 Entry 1509 26E, 1992.
Meanwell et al Chem ABSR vol. 120 p. 1036 Entry 1915854, 1994.

*Primary Examiner*—Richard L. Raymond
*Attorney, Agent, or Firm*—Oblon, Spivak, McClelland, Maier & Neustadt, P.C.

[57] ABSTRACT

Heterocyclic compounds of the formula:

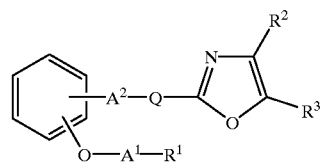

wherein $R^1$ is carboxy or protected carboxy, $R^2$ is aryl which may have suitable substituent(s), $R^3$ is aryl which may have suitable substituent(s), $A^1$ is lower alkylene, $A^2$ is bond or lower alkylene and -Q- is

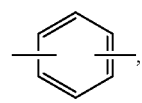

etc., and pharmaceutically acceptable salts thereof which are useful as a medicament.

19 Claims, No Drawings

4,5-DIARYLOXAZOLE DERIVATIVES

This application is a Continuation of application Ser. No. 08/646,261, filed on Jul. 18, 1996, now abandoned, which was filed as an International Application PCT/JP94/02116 filed Dec. 16, 1994.

TECHNICAL FIELD

This invention relates to new heterocyclic compounds and pharmaceutically acceptable salts thereof which are useful as a medicament.

BACKGROUND ART

Some heterocyclic compounds have been known as described, for example, in EP 0434034A1.

DISCLOSURE OF INVENTION

This invention relates to new heterocyclic compounds. More particularly, this invention relates to new heterocyclic compounds and pharmaceutically acceptable salts thereof which have pharmacological activities such as an inhibitory activity on platelet aggregation, vasodilating activity, antihypertensive activity or the like and are prostaglandin $I_2$ agonists, to processes for their production, to a pharmaceutical composition containing the same and to a use thereof for manufacture of medicaments.

Accordingly, one object of this invention is to provide new and useful heterocyclic compounds and pharmaceutically acceptable salts thereof.

Another object of this invention is to provide processes for production of the heterocyclic compounds and salts thereof.

A further object of this invention is to provide a pharmaceutical composition containing, as an active ingredient, said heterocyclic compounds or pharmaceutically acceptable salts thereof.

Still further object of this invention is to provide use of the heterocyclic compounds and pharmaceutically acceptable salts thereof for manufacture of medicaments for the therapeutic and/or prophylactic treatment of arterial obstruction, cerebrovascular disease, hepatic cirrhosis, arteriosclerosis, ischemic heart disease, restenosis after percutaneous transiuminal coronary angioplasty, hypertension or the like.

The heterocyclic compounds of this invention can be represented by the following formula (I):

(I)

wherein
  $R^1$ is carboxy or protected carboxy,
  $R^2$ is aryl which may have suitable substituent(s),
  $R^3$ is aryl which may have suitable substituent(s),
  $A^1$ is lower alkylene,
  $A^2$ is bond or lower alkylene and -Q- is (in which is cyco(lower)alkane or cyclo(lower alkene, each of which may have suitable substituent(s)).

According to the present invention, the new heterocyclic compounds (I) can be prepared by the processes which are illustrated in the following scheme.

Process 1

(II) or a salt thereof  +  $X^1$—$A^1$—$R^1$  ⟶  (III) or a salt thereof (I) or a salt thereof Process 2

(Ia) or a salt thereof

↓ Elimination reation of the carboxy protective group (Ib) or a salt thereof

Process 3
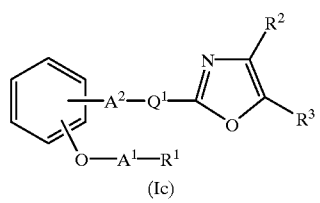
(Ic)
or a salt thereof
↓ oxidation
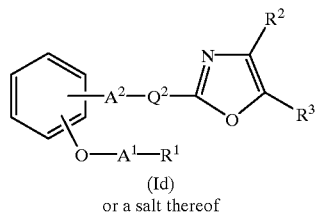
(Id)
or a salt thereof
Process 4
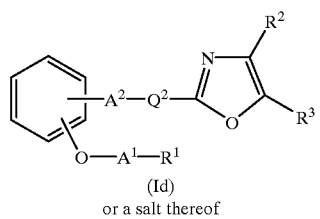
(Id)
or a salt thereof
↓ Reduction
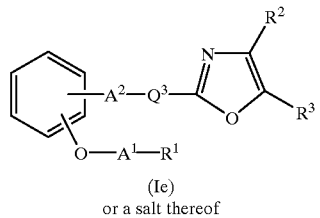
(Ie)
or a salt thereof
Process 5
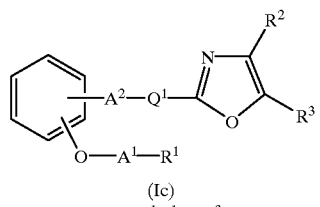
(Ic)
or a salt thereof
↓ Reduction
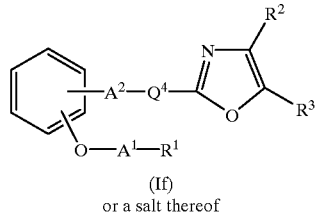
(If)
or a salt thereof
Process 6
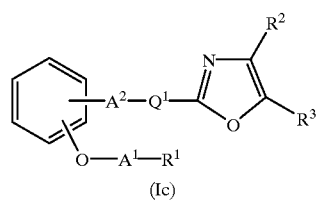
(Ic)
or a salt thereof
↓ Oxidation
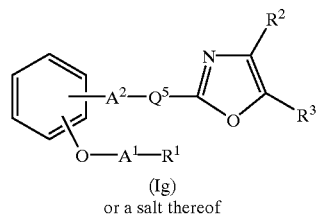
(Ig)
or a salt thereof
Process 7
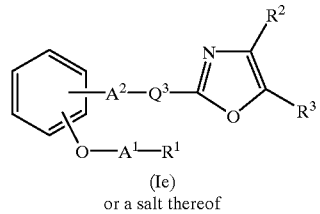
(Ie)
or a salt thereof
↓ Alkylation
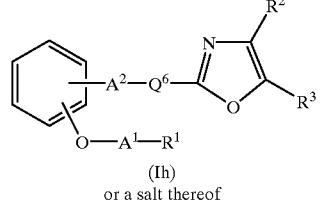
(Ih)
or a salt thereof
Process 8
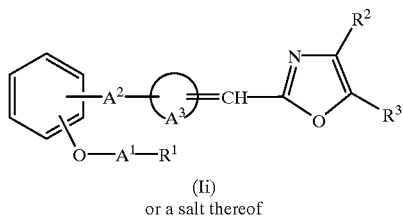
(Ii)
or a salt thereof
↓ Reduction
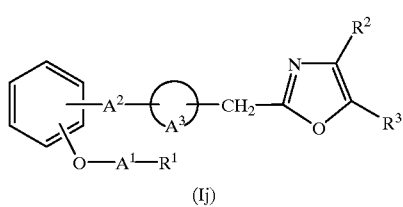
(Ij)
or a salt thereof wherein $R^1$, $R^2$, $R^3$, $A^1$, $A^2$, -Q-, and

are each as defined above, $X^1$ is an acid residue,
$R_a^1$ is protected carboxy,
-$Q^1$- is

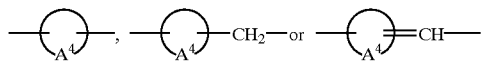

(in which

is cyclo(lower)alkene),
-$Q^2$- is

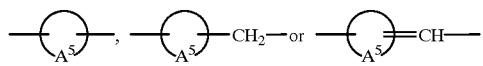

in which

is cyclo(lower)alkalane having an epoxy group),
-$Q^3$- is

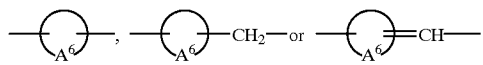

(in which

is cyclo(lower)alkane having a hydroxy group),
-$Q^4$- is

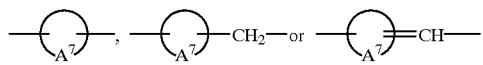

(in which

is cyclo(lower)alkane),

-$Q^5$- is

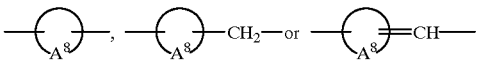

(in which

is cyclo(lower)alkane having two hydroxy groups), and
-$Q^6$- is

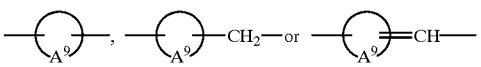

(in which

is cyclo(lower)alkane having a lower alkoxy group).

The starting compound (II) is novel and can be prepared by the following processes.

Process A

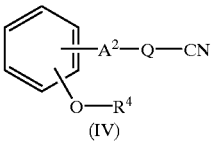
(IV)
or a salt thereof (1) Hydrolysis

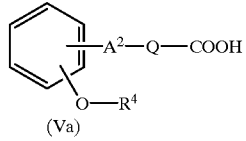
(Va)
or a salt thereof (2) $HO-CH(R^3)-C(=O)-R^2$
(VI)
or a salt thereof

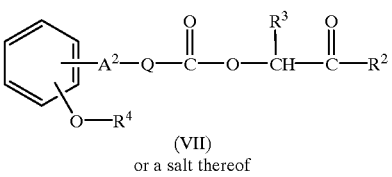
(VII)
or a salt thereof (3) $NH_3$
(VIII)
or a salt thereof

-continued

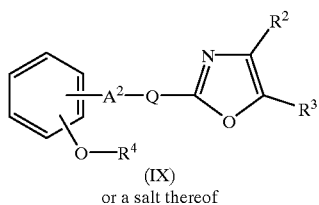
(IX)
or a salt thereof

Process B

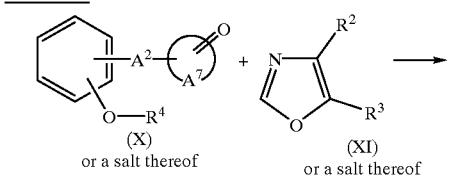
(X)
or a salt thereof
(XI)
or a salt thereof

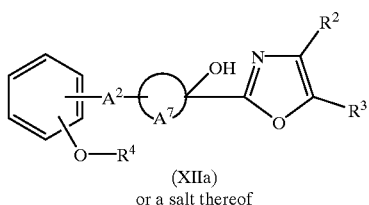
(XIIa)
or a salt thereof

Process C

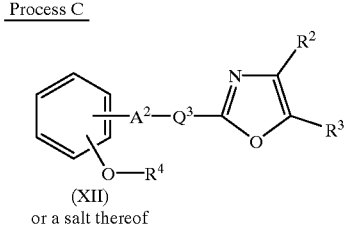
(XII)
or a salt thereof

↓ Dehydration

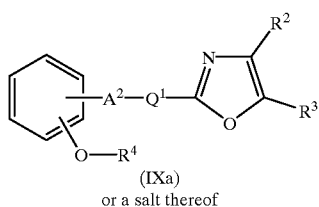
(IXa)
or a salt thereof

Process D

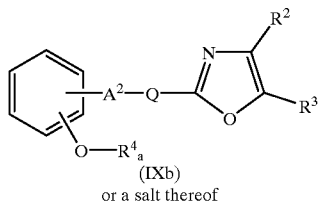
(IXb)
or a salt thereof

↓ Dealkylation

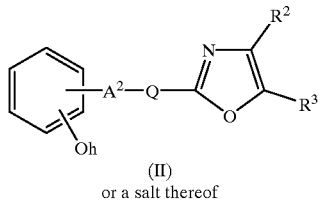
(II)
or a salt thereof

-continued

Process E

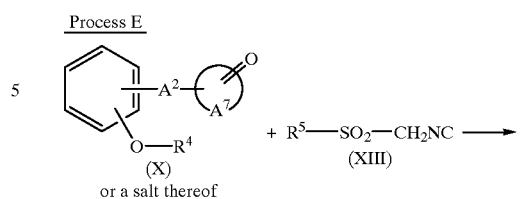
(X)
or a salt thereof
+ $R^5$—$SO_2$—$CH_2NC$ →
(XIII)

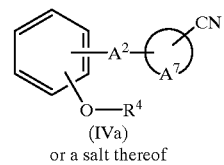
(IVa)
or a salt thereof

Process F

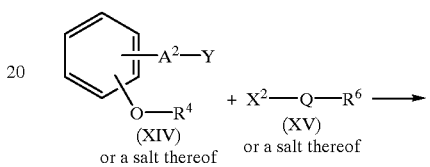
(XIV)
or a salt thereof
+ $X^2$—Q—$R^6$ →
(XV)
or a salt thereof

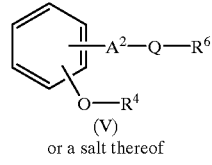
(V)
or a salt thereof

Process G

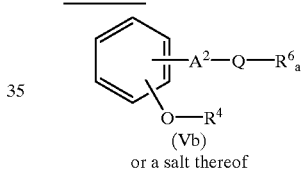
(Vb)
or a salt thereof

↓ Elimination reaction of the carboxy protective group

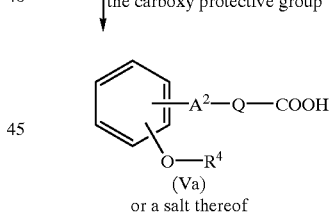
(Va)
or a salt thereof

Process H

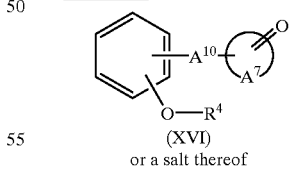
(XVI)
or a salt thereof

↓ Reduction

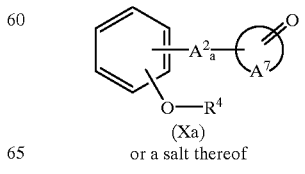
(Xa)
or a salt thereof

Process I

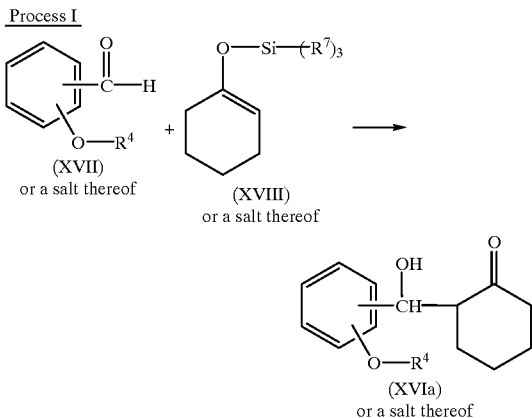

(XVII) or a salt thereof  +  (XVIII) or a salt thereof  →  (XVIa) or a salt thereof wherein
$R^2$, $R^3$, $A^2$,

-Q-, -$Q^1$- and -$Q^3$- are each as defined above,
$R^4$ is hydrogen or lower alkyl,
$R_a^4$ is lower alkyl,
Y is halogen,
$X^2$ is an acid residue,
$R^5$ is aryl which may have suitable substituent(s),
$R^6$ is carboxy or protected carboxy,
$R_a^6$ is protected carboxy,
$A^{10}$ is lower alkylene having a hydroxy group,
$A_a^2$ is lower alkylene, and
$R^7$ is lower alkyl.

Suitable pharmaceutically acceptable salts of the object compound (I) are conventional non-toxic salts and include a metal salt such as an alkali metal salt (e.g. sodium salt, potassium salt, etc.) and an alkaline earth metal salt (e.g. calcium salt, magnesium salt, etc.), an ammonium salt, an organic base salt (e.g. trimethylamine salt, triethylamine salt, pyridine salt, picoline salt, dicyclohexylamine salt, N,N'-dibenzylethylenediamine salt, etc.), an organic acid salt (e.g. acetate, maleate, tartrate, methanesulfonate, benzenesulfonate, formate, toluenesulfonate, trifluoroacetate, etc.), an inorganic acid salt (e.g. hydrochloride, hydrobromide, sulfate, phosphate, etc.), a salt with an amino acid (e.g. arginine, aspartic acid, glutamic acid, etc.), and the like.

In the above and subsequent descriptions of the present specification, suitable examples and illustrations of the various definitions which the present invention include within the scope thereof are explained in detail as follows.

The term "lower" is intended to mean 1 to 6 carbon atom(s), unless otherwise indicated.

Suitable "aryl" may include phenyl, naphthyl and the like.

Suitable "lower alkylene" may include straight or branched one having 1 to 6 carbon atom(s), such as methylene, ethylene, trimethylene, tetramethylene, pentamethylene, hexamethylene or the like, preferably one having 1 to 3 carbon atom(s).

Suitable "lower alkyl" may include straight or branched one having 1 to 6 carbon atom(s), such as methyl, ethyl, propyl, isopropyl, butyl, isobutyl, sec-butyl, t-butyl, pentyl, t-pentyl, hexyl or the like, preferably one having 1 to 4 carbon atom(s).

Suitable "protected carboxy" may include esterified carboxy and the like.

Suitable example of the ester moiety of an esterified carboxy may be the ones such as lower alkyl ester (e.g. methyl ester, ethyl ester, propyl ester, isopropyl ester, butyl ester, isobutyl ester, tert-butyl ester, pentyl ester, hexyl ester, etc.) which may have at least one suitable substituent(s), for example, lower alkanoyloxy(lower)alkyl ester (e.g. acetoxymethyl ester, propionyloxymethyl ester, butyryloxymethyl ester, valeryloxymethyl ester, pivaloyloxymethyl ester, hexanoyloxymethyl ester, 1(or 2)-acetoxyethyl ester, 1(or 2 or 3)-acetoxypropyl ester, 1(or 2 or 3 or 4)-acetoxybutyl ester, 1(or 2)-propionyloxyethyi ester, 1(or 2 or 3)-propionyloxypropyl ester, 1(or 2)-butyryloxyethyl ester, 1(or 2)-isobutyryloxyethyl ester, 1(or 2)-pivaloyloxyethyl ester, 1(or 2)-hexanoyloxyethyl ester, isobutyryloxymethyl ester, 2-ethylbutyryloxymethyl ester, 3,3-dimethylbutyryloxymethyl ester, 1(or 2)-pentanoyloxyethyl ester, etc.], lower alkylsulfonyl(lower) alkyl ester (e.g. 2-mesylethyl ester, etc.), mono(or di or tri)-halo(lower)alkyl ester (e.g. 2-iodoethyl ester, 2,2,2-trichloroethyl ester, etc.), lower alkoxycarbonyloxy(lower) alkyl ester (e.g. methoxycarbonyloxymethyl ester, ethoxycarbonyloxymethyl ester, 2-methoxycarbonyloxyethyl ester, 1-ethoxycarbonyloxyethyl ester, 1-isopropoxycarbonyloxyethyl ester, etc.), phthalidylidene (lower)alkyl ester, or (5-lower alkyl 2-oxo-1,3-dioxol-4-yl) (lower)alkyl ester [e.g. (5-methyl-2-oxo-1,3-dioxol-4-yl) methyl ester, (5-ethyl-2-oxo-1,3-dioxol-4-yl)methyl ester, (5-propyl-2-oxo-1,3-dioxol-4-yl)ethyl ester, etc.]; lower alkenyl ester (e.g. vinyl ester, allyl ester, etc.); lower alkynyl ester (e.g. ethynyl ester, propynyl ester, etc.); ar(lower)alkyl ester which may have at least one suitable substituent(s) such as mono(or di or tri)-phenyl(lower)alkyl ester which may have at least one suitable substituent(s) (e.g. benzyl ester, 4-methoxybenzyl ester, 4-nitrobenzyl ester, phenethyl ester, trityl ester, benzhydryl ester, bis(methoxyphenyl) methyl ester, 3,4-dimethoxybenzyl ester, 4-hydroxy-3,5-di-tert-butylbenzyl ester, etc.); aryl ester which may have at least one suitable substituent(s) (e.g. phenyl ester, 4-chlorophenyl ester, tolyl ester, tert-butylphenyl ester, xylyl ester, mesityl ester, cumenyl ester, etc.); phthalidyl ester; and the like.

Suitable "substituent" in the term "aryl which may have suitable substituent(s)" may include halogen, amino, hydroxy, lower alkoxy, lower alkyl as exemplified above, and the like.

Suitable "cyclo(lower)alkane" may include cyclopropane, cyclobutane, cyclopentane and cyclohexane.

Suitable "cyclo(lower)alkene" may include cyclopropene, cyclobutene, cyclopentene and cyclohexene.

Suitable "substituent" in the term "cyclo(lower)alkane or cyclo(lower)alkene, each of which may have suitable substituent(s)" may include epoxy, hydroxy, lower alkoxy and the like.

Suitable "lower alkoxy" may include methoxy, ethoxy, propoxy, isopropoxy, butoxy, isobutoxy, t-butoxy, pentyloxy, t-pentyloxy, hexyloxy and the like.

Suitable "acid residue" may include halogen (e.g. chlorine, bromine, iodine, etc.), lower alkanoyloxy (e.g. acetyloxy, etc.), sulfonyloxy (e.g. methylsulfonyloxy, phenylsulfonyloxy, tolylsulfonyloxy, etc.), and the like.

Suitable "halogen" may include the ones as exemplified above.

Preferred embodiments of the object compound (I) are as follows:

$R^1$ is carboxy, or protected carboxy (more preferably esterified carboxy, most preferably lower alkoxycarbonyl, $R^2$ is aryl which may have one to three (more preferably one) suitable substituent(s) [more preferably phenyl or lower alkylphenyl], $R^3$ is aryl which may have one to three (more preferably one) suitable substituent(s) [more preferably phenyl or lower alkylphenyl], $A^1$ is lower alkylene (more preferably $C_1$–$C_3$ alkylene, most preferably methylene), $A^2$ is bond, or lower alkylene (more preferably $C_1$–$C_3$ alkylene, most preferably methylene), and -Q- is

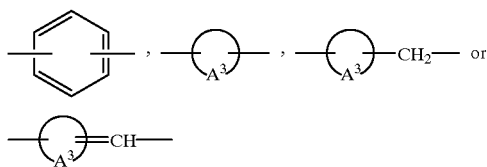

(in which

is cyclo(lower)alkane or cyclo(lower)alkene, each of which may have one to three (more preferably one or two) suitable substituent(s) (more preferably substituent(s) selected from the group consisting of epoxy, hydroxy and lower alkoxy)).

More preferred embodiments of the object compound (I) are as follows:

$R^1$ is carboxy, or protected carboxy (more preferably esterified carboxy, most preferably lower alkoxycarbonyl), $R^2$ is aryl which may have one to three (more preferably one) suitable substituent(s) [more preferably phenyl or lower alkylphenyl], $R^3$ is aryl which may have one to three (more preferably one) suitable substituent(s) [more preferably phenyl or lower alkylphenyl], $A^1$ is lower alkylene (more preferably $C_1$–$C_3$ alkylene, most preferably methylene), $A^2$ is bond, or lower alkylene (more preferably $C_1$–$C_3$ alkylene, most preferably methylene), and -Q- is

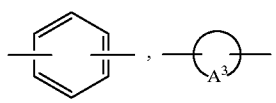

(in which

is cyclo(lower)alkane which may have a substituent selected from the group consisting of epoxy, hydroxy and lower alkoxy, or cyclo(lower)alkene),

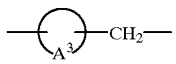

(in which

is cyclo(lower)alkane which may have one or two substituent(s) selected from the group consisting of epoxy and hydroxy, or cyclo(lower)alkene), or

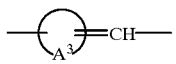

(in which

is cyclo(lower)alkane).

The processes for preparing the object and starting compounds of the present invention are explained in detail in the following.

PROCESS 1

The compound (I) or a salt thereof can be prepared by reacting the compound (II) or a salt thereof with the compound (III) or a salt thereof.

This reaction is usually carried out in a solvent such as acetonitrile, benzene, N,N-dimethylformamide, tetrahydrofuran, methylene chloride, ethylene chloride, chloroform, diethyl ether or any other solvent which does not adversely affect the reaction.

The reaction temperature is not critical and the reaction is usually carried out under cooling to warming.

The reaction is usually carried out in the presence of a base.

Suitable base may include the inorganic base such as alkali metal hydroxide (e.g. sodium hydroxide, potassium hydroxide, etc.), alkaline earth metal hydroxide (e.g. magnesium hydroxide, calcium hydroxide, etc.), alkali metal carbonate (e.g. sodium carbonate, potassium carbonate, etc.), alkaline earth metal carbonate (e.g. magnesium carbonate, calcium carbonate, etc.) or the like, and the organic base such as tri(lower)alkylamine (e.g., trimethylamine, triethylamine, diisopropylethylamine, etc.), di(lower)alkylaniline (e.g. dimethylaniline, etc.), pyridine or the like.

PROCESS 2

The compound (Ib) or a salt thereof can be prepared by subjecting the compound (Ia) or a salt thereof to elimination reaction of the carboxy protective group.

Suitable method of this reaction may include conventional one such as hydrolysis, reduction and the like.

(i) For Hydrolysis

The hydrolysis is preferably carried out in the presence of a base or an acid including Lewis acid.

Suitable base may include an inorganic base and an organic base such as an alkali metal [e.g. sodium, potassium, etc.], the hydroxide or carbonate or bicarbonate thereof, trialkylamine [e.g. trimethylamine, triethylamine, etc.], picoline, 1,5-diazabicyclo[4.3.0]-non-5-ene, 1,4-diazabicyclo[2.2.2]octane, 1,8-diazabicyclo[5.4.0]undec-7-ene, or the like.

Suitable acid may include an organic acid [e.g. formic acid, acetic acid, propionic acid, trichloroacetic acid, trifluoroacetic acid, etc.] and an inorganic acid [e.g. hydrochloric acid, hydrobromic acid, sulfuric acid, hydrogen chloride, hydrogen bromide, etc.]. The elimination using Lewis acid such as trihaloacetic acid [e.g. trichloroacetic acid, trifluoroacetic acid, etc.] or the like is preferably carried out in the presence of cation trapping agents [e.g. anisole, phenol, etc.].

The reaction is usually carried out in a solvent such as water, an alcohol [e.g. methanol, ethanol, etc.], methylene chloride, tetrahydrofuran, 1,2-dimethoxyethane, a mixture thereof or any other solvent which does not adversely influence the reaction. A liquid base or acid can be also used as the solvent. The reaction temperature is not critical and the reaction is usually carried out under cooling to warming.

(ii) For reduction:

Reduction is carried out in a conventional manner, including chemical reduction and catalytic reduction.

Suitable reducing agents to be used in chemical reduction are a combination of a metal (e.g. tin, zinc, iron, etc.) or metallic compound (e.g. chromium chloride, chromium acetate, etc.) and an organic or inorganic acid (e.g. formic acid, acetic acid, propionic acid, trifluoroacetic acid, p-toluenesulfonic acid, hydrochloric acid, hydrobromic acid, etc.).

Suitable catalysts to be used in catalytic reduction are conventional ones such as platinum catalysts (e.g. platinum plate, spongy platinum, platinum black, colloidal platinum, platinum oxide, platinum wire, etc.), palladium catalysts (e.g. spongy palladium, palladium black, palladium oxide, palladium on carbon, colloidal palladium, palladium on barium sulfate, palladium on barium carbonate, etc.), nickel catalysts (e.g. reduced nickel, nickel oxide, Raney nickel, etc.), cobalt catalysts (e.g. reduced cobalt, Raney cobalt, etc.), iron catalysts (e.g. reduced iron, Raney iron, etc.), copper catalysts (e.g. reduced copper, Raney copper, Ullman copper, etc.) and the like. The reduction is usually carried out in a conventional solvent which does not adversely influence the reaction such as water, methanol, ethanol, propanol, ethyl acetate, N,N-dimethylformamide, tetrahydrofuran, or a mixture thereof. Additionally, in case that the above-mentioned acids to be used in chemical reduction are in liquid, they can also be used as a solvent.

The reaction temperature of this reduction is not critical and the reaction is usually carried out under cooling to warming.

PROCESS 3

The compound (Id) or a salt thereof can be prepared by subjecting the compound (Ic) or a salt thereof to oxidation reaction.

Oxidation is carried out in a conventional manner and suitable oxidizing reagent may include per acid (e.g., perbenzoic acid, m-chloroperbenzoic acid, performic acid, peracetic acid, perphthalic acid, etc.), and the like.

The reaction is usually carried out in a conventional solvent such as water, alcohol, (e.g., methanol, ethanol, isopropyl alcohol, etc.), tetrahydrofuran, dioxane, dichloromethane, ethylene dichloride, chloroform, N,N-dimethylformamide, N,N-dimethylacetamide, or any other organic solvent which does not adversely affect the reaction.

The reaction temperature is not critical and the reaction is usually carried out under cooling to heating.

PROCESS 4

The compound (Ie) or a salt thereof can be prepared by subjecting the compound (Id) or a salt thereof to reduction reaction.

This reduction can be carried out in a similar manner to that of the aforementioned Process 2, and therefore the reagents to be used and the reaction conditions (e.g., solvent, reaction temperature, etc.) can be referred to those of the Process 2.

PROCESS 5

The compound (If) or a salt thereof can be prepared by subjecting the compound (Ic) or a salt thereof to reduction reaction.

This reduction can be carried out in a similar manner to that of the aforementioned Process 2, and therefore the reagents to be used and the reaction conditions (e.g., solvent, reaction temperature, etc.) can be referred to those of the Process 2.

PROCESS 6

The compound (Ig) or a salt thereof can be prepared by subjecting the compound (Ic) or a salt thereof to oxidation reaction.

This oxidation can be carried out in a similar manner to that of the aforementioned Process 3, and therefore the reagents to be used and the reaction conditions (e.g., solvent, reaction temperature, etc.) can be referred to those of the Process 3.

PROCESS 7

The compound (Ih) or a salt thereof can be prepared by subjecting the compound (Ie) or a salt thereof to alkylation reaction.

This reaction can be carried out in accordance with the method disclosed in the Example 20 described later or a similar manner thereto.

PROCESS 8

The compound (Ij) or a salt thereof can be prepared by subjecting the compound (Ii) or a salt thereof to reduction reaction.

This reduction can be carried out in a similar manner to that of the aforementioned Process 2, and therefore the reagents to be used and the reaction conditions (e.g., solvent, reaction temperature, etc.) can be referred to those of the Process 2.

PROCESS A-①

The compound (Va) or a salt thereof can be prepared by subjecting the compound (IV) or a salt thereof to hydrolysis reaction.

This reaction can be carried out in accordance with the method disclosed in the Preparation 2 described later or a similar manner thereto.

PROCESS A-②

The compound (VII) or a salt thereof can be prepared by reacting the compound (Va) or a salt thereof with the compound (VI) or a salt thereof.

This reaction can be carried out in accordance with the method disclosed in the Preparation 3 described later or a similar manner thereto.

PROCESS A-③

The compound (IX) or a salt thereof can be prepared by reacting the compound (VII) or a salt thereof with the compound (VIII) or a salt thereof.

This reaction can be carried out in accordance with the method disclosed in the Preparation 4 described later or a similar manner thereto.

PROCESS B

The compound (XIIa) or a salt thereof can be prepared by reacting the compound (X) or a salt thereof with the compound (XI) or a salt thereof.

This reaction can be carried out in accordance with the methods disclosed in the Preparations 6 and 7 described later or similar manners thereto.

PROCESS C

The compound (IXa) or a salt thereof can be prepared by subjecting the compound (XII) or a salt thereof to dehydration reaction.

This reaction can be carried out in accordance with the methods disclosed in the Preparations 8 and 9 described later or similar manners thereto.

PROCESS D

The compound (II) or a salt thereof can be prepared by subjecting the compound (IXb) or a salt thereof to dealkylation reaction.

The reagent to be used in this reaction may include halotrialkylsilane (e.g., iodotrimethylsilane, etc.), alkali metal thioalkoxide (e.g., sodium thioethoxide, etc.), alkali metal sulfide (e.g., sodium sulfide, etc.), alkali metal diphenylphosphide (e.g., lithium diphenylphosphide, etc.), aluminum halide (e.g., aluminum chloride, aluminum bromide, etc.), boron trihalide (e.g., boron trichloride, boron tribromide, etc.), pyridine hydrochloride, alkylmagnesium halide (e.g., methylmagnesium iodide, etc.), lithium halide (e.g., lithium chloride, etc.), and the like.

The reaction is usually carried out in a conventional solvent such as water, alcohol, (e.g., methanol, ethanol, isopropyl alcohol, etc.), tetrahydrofuran, dioxane, dichloromethane, ethylene dichloride, chloroform, N,N-dimethylformamide, N,N-dimethylacetamide, or any other organic solvent which does not adversely affect the reaction.

The reaction temperature is not critical and the reaction is usually carried out under cooling to heating.

PROCESS E

The compound (IVa) or a salt thereof can be prepared by reacting the compound (X) or a salt thereof with the compound (XIII).

This reaction can be carried out in accordance with the method disclosed in the Preparation 1 described later or a similar manner thereto.

PROCESS F

The compound (V) or a salt thereof can be prepared by reacting the compound (XIV) or a salt thereof with the compound (XV) or a salt thereof.

This reaction can be carried out in accordance with the method disclosed in the Preparation 28 described later or a similar manner thereto.

PROCESS G

The compound (Va) or a salt thereof can be prepared by subjecting the compound (Vb) or a salt thereof to elimination reaction of the carboxy protective group.

This reduction can be carried out in a similar manner to that of the aforementioned Process 2, and therefore the reagents to be used and the reaction conditions (e.g., solvent, reaction temperature, etc.) can be referred to those of the Process 2.

PROCESS H

The compound (Xa) or a salt thereof can be prepared by subjecting the compound (XVI) or a salt thereof to reduction reaction.

This reduction can be carried out in a similar manner to that of the aforementioned Process 2, and therefore the reagents to be used and the reaction conditions (e.g., solvent, reaction temperature, etc.) can be referred to those of the Process 2.

PROCESS I

The compound (XVIa) or a salt thereof can be prepared by reacting the compound (XVII) or a salt thereof with the compound (XVIII) or a salt thereof.

This reaction can be carried out in accordance with the method disclosed in the Preparation 43 described later or a similar manner thereto.

The object compound (I) of this invention and pharmaceutically acceptable salt thereof have pharmacological activities such as an inhibitory activity on platelet aggregation, vasodilating activity, antihypertensive activity or the like and are prostaglandin $I_2$ agonists, and therefore can be used for treating and/or preventing arterial obstruction (e.g., chronic arterial obstruction, etc.), cerebrovascular disease, gastric ulcer, hepatitis, hepatic insufficiency, hepatic cirrhosis, arteriosclerosis, ischemic heart disease, restenosis after percutaneous transluminal coronary angioplasty, hypertension, inflammation, heart failure, renal disease (e.g., renal failure, nephritis, etc.), diabetic neuropathy, diabetic nephropathy, peripheral circulatory disturbance, and the like, and can be also used for protecting organs after transplantation.

In order to show the utility of the object compound (I), pharmacological data of the representative compound thereof are shown in the following.

i) Inhibition of human platelet aggregation induced by ADP

[I] Test Compound:

Isomer C obtained in Example 2.

[II] Test method:

Human blood was obtained from healthy volunteers and mixed with 1/10 volume of 3.8% sodium citrate, pH 7.4. The citrate blood was centrifuged at 150×g for 10 minutes and the platelet rich plasma (PRP) was removed. The remaining blood was centrifuged for a further 10 minutes at 1500×g to prepare the platelet poor plasma (PPP), which was used as a reference for platelet aggregation. Aggregation studies were carried out using HEMATRACER 801 (NBS, Japan), a 8 channel aggregometer. 25 µl sample solution and 225 µl of PRP were mixed and stirred at 1000 rpm for 2 minutes at 37° C. Aggregation was induced by ADP solution at the final concentration of 2.5 µM.

[III] Test result:

| Test Compound | Inhibition (%) |
|---|---|
| $3.2 \times 10^{-7}$M | $100 \pm 0.4$ | mean ± S.E.

ii) Effect on mean arterial blood pressure in conscious rats

[I] Test Compound:

Sodium [3-[[(1S)-2-(4,5-diphenyloxazol-2-yl)-2-cyclohexen-1-yl]methyl]phenoxy]acetate

[II] Test Method:

Male Sprague-Dawley rats, aged 8–9 weeks, were anesthetized with diethyl ether and a polyethylene cannula filled with heparin solution was inserted into the femoral artery of the rats to measure mean blood pressure. Mean blood pressure was measured with a pressure transducer and recorded on a polygraph. Two hours after operation, the test compound suspended in 0.5% methyl cellulose was administered orally in a volume of 5 ml/kg. Oral hypotensive effect of the test compound was expressed as the maximal decrease (R max). Briefly, R max was expressed as maximal % change compared to mean blood pressure prior to the administration of the test compound.

[III] Test Result:

| Test Compound | R max (%) |
|---|---|
| 3.2 mg/kg | 31.3 |

The pharmaceutical composition of the present invention can be used in the form of a pharmaceutical preparation, for example, in solid, semisolid or liquid form (e.g. tablet, pellet, troche, capsule, suppository, cream, ointment, aerosol, powder, solution, emulsion, suspension etc.), which contains the object compound (I) or a pharmaceutically acceptable salt thereof as an active ingredient, suitable for rectal, pulmonary (nasal or buccal inhalation), nasal, ocular, external (topical), oral or parenteral (including subcutaneous, intravenous and intramuscular) administrations or insufflation.

The pharmaceutical composition of this invention can contain various organic or inorganic carrier materials, which are conventionally used for pharmaceutical purpose, such as excipient (e.g. sucrose, starch, mannit, sorbit, lactose, glucose, cellulose, talc, calcium phosphate, calcium carbonate, etc.), binding agent (e.g. cellulose, methyl cellulose, hydroxypropylcellulose, polypropylpyrrolidone, gelatin, gum arabic, polyethyleneglycol, sucrose, starch, etc.), disintegrator (e.g. starch, carboxvmethyl cellulose, calcium salt of carboxymethyl cellulose, hydroxypropylstarch, sodium glycol-starch, sodium bicarbonate, calcium phosphate, calcium citrate, etc.), lubricant (e.g. magnesium stearate, talc, sodium laurylsulfate, etc.), flavoring agent (e.g. citric acid, mentol, glycine, orange powders, etc.), preservative (e.g. sodium benzoate, sodium bisulfite, methylparaben, propylparaben, etc.), stabilizer (e.g. citric acid, sodium citrate, acetic acid, etc.), suspending agent (e.g. methyl cellulose, polyvinylpyrrolidone, aluminum stearate, etc.), dispersing agent, aqueous diluting agent (e.g. water), base wax (e.g. cacao butter, polyethyleneglycol, white petrolatum, etc.).

The effective ingredient may usually be administered with a unit dose of 0.01 mg/kg to 50 mg/kg, 1 to 4 times a day. However, the above dosage may be increased or decreased according to age, weight, conditions of the patient or the administering method.

The following preparations and examples are given only for the purpose of illustrating the present invention in more detail.

PREPARATION 1

A solution of potassium tert-butoxide (4.10 g) in tert-butanol-1,2-dimethoxyethane (1:1, 38 ml) was added dropwise to a stirred solution of 2-[(3-methoxyphenyl)-methyl]cyclohexanone (4.10 g) and (p-tolylsulfonyl)methyl isocyanide (4.10 g) in 1,2-dimethoxyethane under ice cooling over 30 minutes. The resulting mixture was stirred at the same temperature for 1 hour and at room temperature for 2 hours and 30 minutes, and then a mixture of diethyl ether and water was added thereto. The organic layer was separated, washed with water and brine, dried over magnesium sulfate, and evaporated in vacuo. The oily residue was chromatographed over silica gel using n-hexane—ethyl acetate as an eluent to afford 1-cyano-2-[(3-methoxyphenyl)methyl]cyclohexane (3.73 g) as an oil.

IR (Film) : 2224, 1260 cm$^{-1}$

NMR (CDCl$_3$, δ) : 0.9–1.7 (16H, m), 1.8–2.7 (m) +3.10 (dd, J=3.5Hz, 13.4Hz) +3.35 (m) total 8H, 3.79 (3H, s), 3.80 (3H, s), 6.7–6.8 (6H, m), 7.1–7.3 (2H, m)

(+) APCI Mass (m$^+$/z) : 230 (M$^+$+1)

PREPARATION 2

A solution of 1-cyano-2-[(3-methoxyphenyl)methyl]-cyclohexane (3.60 g) and potassium hydroxide (2.82 g) in ethyleneglycol (12.3 ml) was refluxed for 5 hours, cooled to room temperature, and diluted with water and 5% sodium hydroxide aqueous solution. The resulting mixture was washed three times with diethyl ether, acidified with conc. hydrochloric acid, and extracted with diethyl ether. The extract was dried over magnesium sulfate and evaporated in vacuo to give 2-[(3-methoxyphenyl)-methyl]cyclohexanecarboxylic acid (3.11 g) as an oil.

IR (Film) : 2750–2350, 1700, 1260 cm$^{-1}$

NMR (CDCl$_3$, δ) : 0.8–2.3 (m) +2.6–2.9 (m) total 24H, 3.8 (6H, s), 6.6–6.7 (6H, m), 7.0–7.3 (2H, m)

(−) APCI Mass (m$^+$/z) 247 (M$^+$−1)

PREPARATION 3

1-Ethyl-3-(3-dimethylaminopropyl)carbodiimide hydrochloride (501 mg) was added to a stirred solution of 2-[(3-methoxyphenyl)methyl]cyclohexanecarboxylic acid (500 mg), benzoin (427 mg), and 4-dimethylaminopyridine (12.2 mg) in dichloromethane (10 ml) under ice cooling. The resulting mixture was stirred at the same temperature for 2 hours and at room temperature for 1 hour, and then a mixture of ethyl acetate and 1N hydrochloric acid was added thereto. The organic layer was separated, washed successively with 1N hydrochloric acid, sodium bicarbonate aqueous solution and brine, dried over magnesium sulfate, and evaporated in vacuo. The residue was chromatographed over silica gel using n-hexane—toluene as an eluent to afford 2-oxo-1,2-diphenylethyl 2-[(3-methoxyphenyl)-methyl]cyclohexanecarboxylate (455 mg) as a colorless oil.

IR (Film) : 1725, 1690 cm$^{-1}$

NMR (CDCl$_3$, δ) : 0.9–2.3 (40H, broad), 2.5–3.0 (8H, m), 3.6–3.8 (12H, m), 6.59–6.61 (m) +6.68–6.76 (m) total 12H, 6.8–6.9 (4H, m), 7.0–7.5 (36H, m), 7.9–8.0 (8H, m)

(+) APCI Mass (m$^+$/z) : 433 (M$^+$+1)

PREPARATION 4

A solution of 2-oxo-1,2-diphenylethyl 2-[(3-methoxyphenyl)methyl]cyclohexanecarboxylate (440 mg) and ammonium acetate (593 mg) in acetic acid (2.4 ml) was refluxed for 3 hours and cooled to room temperature, and a mixture of water and dichloromethane was added thereto. The organic layer was washed with water and sodium bicarbonate aqueous solution, dried over magnesium sulfate, and evaporated in vacuo to afford 2-[2-[(3-methoxyphenyl) methyl]cyclohexyl]-4,5-diphenyloxazole (394 mg).

IR (Film) : 1600, 1260 cm$^{-1}$

NMR (CDCl$_3$, δ) : 1.0–1.8 (14H, broad), 2.0–2.4 (broad) +2.5–2.8 (broad) +3.2–3.3 (m) total 10H, 6.6–6.7 (6H, m), 7.1 (2H, m), 7.3–7.4 (12H, m), 7.5–7.7 (8H, m)

(+) APCI Mass (m$^+$/z) 424 (M$^+$+1)

PREPARATION 5

1.0 M Solution of boron tribromide in dichloromethane (1.25 ml) was added dropwise to a stirred solution of 2-[2-[(3-methoxyphenyl)methyl]cyclohexyl]-4,5-diphenyloxazole (370 mg) in dichloromethane (2.0 ml) under ice cooling. The resulting mixture was stirred at the same temperature for 2 hours and at room temperature for 22 hours, and then a mixture of ethyl acetate and sodium bicarbonate aqueous solution was added thereto. The organic layer was washed with sodium bicarbonate aqueous solution and brine, dried over magnesium sulfate, and evaporated in vacuo. The oily residue was chromatographed over silica gel using n-hexane—ethyl acetate as an eluent to afford 2-[2-[(3-hydroxyphenyl)methyl]-cyclohexyl]-4,5-diphenyloxazole (303 mg) as a syrup.

NMR (CDCl$_3$, δ) : 0.8–1.1 (2H, m), 1.2–1.8 (12H, broad), 2.0–2.8 (m) +3.25–3.28 (m) total 10H, 6.5–6.7 (6H, m), 6.9–7.0 (2H, m), 7.2–7.4 (12H, m), 7.5–7.7 (8H, m)

(+) APCI Mass (m$^+$/z) 410 (M$^+$+1)

PREPARATION 6

To a solution of 4,5-diphenyloxazole in tetrahydrofuran (100 ml) at −78° C. under nitrogen was added n-butyllithium (in hexane, 1,7N, 12 ml). After 30 minutes, at the same temperature a solution of 2-(3-methoxybenzyl) cyclopentanone (3.8 g) in tetrahydrofuran (10 ml) was added dropwise thereto. After being stirred for 1 hour at 0° C., the reaction mixture was poured into a mixture of ethyl acetate (200 ml) and 1N-hydrochloric acid (50 ml). The organic layer was washed with saturated sodium bicarbonate aqueous solution and brine, dried over magnesium sulfate, and evaporated in vacuo. The oily residue was chromatographed (n-hexane—ethyl acetate:5:1–2:1) on silica gel to afford 1-hydroxy-1-(4,5-diphenyloxazol-2-yl)-2-(3-methoxybenzyl)cyclopentane (8.0 g).

IR (Neat) : 3350–3400, 1600 cm$^{-1}$

NMR (CDCl$_3$, δ) : 1.25–3.00 (9H, m), 3.57, 3.71 (3H, each s), 6.6–6.8 (3H, m), 7.0–7.8 (11H, m)

Mass (m/e) : 426 (M$^+$+1)

PREPARATION 7

A 1.5 M solution of lithium diisopropylamide mono (tetrahydrofuran) in cyclohexane (19.9 ml) was added dropwise to a stirred solution of 4,5-diphenyloxazole (6.0 g) in tetrahydrofuran (36 ml) and diethyl ether (18 ml) under dry ice—carbon tetrachloride cooling and the mixture was stirred at the same temperature for a while and at 0° C. for a while. A solution of 2-[(3-methoxyphenyl)methyl] cyclohexanone (5.92 g) in tetrahydrofuran (16 ml) was added to the reaction mixture under dry ice-acetone cooling, and the resulting mixture was stirred at the same temperature for several hours. Then the reaction temperature was allowed to rise gradually to room temperature and the reaction mixture was allowed to stand at room temperature overnight. The mixture was treated with ammonium chloride aqueous solution and partitioned between ethyl acetate and 1N hydrochloric acid. The ethyl acetate layer was separated and washed successively with 1N hydrochloric acid (twice), sodium bicarbonate aqueous solution, and brine, dried over magnesium sulfate, and evaporated in vacuo. The oily residue was chromatographed (n-hexane - ethyl acetate (10:1)) over silica gel. The first eluate afforded 2-[(1RS,2RS)-1-hydroxy-2-[(3-methoxyphenyl)methyl]-cyclohexyl]-4,5-diphenyloxazole (4.48 g) as pale yellow paste.

IR (Neat) : 3430, 1590, 1250 cm$^{-1}$

NMR (CDCl$_3$, δ) : 1.5–1.8 (6H, br), 1.91–1.96 (2H, m), 2.25–2.65 (3H, m), 3.22 (1H, s), 3.62 (3H, s), 6.57–6.67 (3H, m), 7.02–7.10 (1H, m), 7.32–7.41 (6H, m), 7.50–7.55 (2H, m), 7.61–7.66 (2H, m)

Mass ((+)APCI) : 440 (M$^+$+1)

The second eluate afforded 2-[(1RS,2SR)-1-hydroxy-2-[(3-methoxyphenyl)methyl]cyclohexyl]-4,5-diphenyloxazole (2.24 g) as pale yellow paste.

IR (Neat) 3410, 1590, 1240 cm$^{-1}$

NMR (CDCl$_3$, δ) : 1.6–1.9 (7H, br), 2.09–2.15 (2H, m), 2.20–2.26 (1H, m), 3.08 (1H, br d, j=9.9Hz), 3.52 (1H, s), 3.75 (3H, s), 6.69–6.76 (3H, m), 7.12–7.20 (1H, m), 7.34–7.45 (6H, m), 7.58–7.72 (4H, m)

Mass ((+)APCI) : 440 (M$^+$+1)

PREPARATION 8

To a solution of 1-hydroxy-1-(4,5-diphenyloxazol-2-yl)-2-(3-methoxybenzyl)cyclopentane (8.0 g) in toluene (160 ml) was added potassium hydrogensulfate (2.6 g), and the solution was stirred for 1 hour under reflux. After being cooled, the solution was washed with water, saturated sodium bicarbonate aqueous solution and brine and evaporated in vacuo. The oily residue was chromatographed on silica gel to afford a mixture (8.0 g) of 1-(4,5-diphenyloxazol-2-yl)-5-(3-methoxybenzyl)-cyclopentene and 1-(4,5-diphenyloxazol-2-yl)-2-(3-methoxybenzyl) cyclopentene.

IR (Neat) : 1590, 1480, 1440 cm$^{-1}$

NMR (CDCl$_3$, δ) : 1.8–2.2 (2H, m), 2.3–2.7 (3H, m), 3.75, 3.77 (3H, each s), 6.6–7.0 (4H, m), 7.1–7.4 (6H, m), 7.5–7.8 (4H, m)

Mass (m/e) : 408 (M$^+$+1)

PREPARATION 9

A suspension of 2-[(1RS,2SR)-1-hydroxy-2-[(3-methoxyphenyl)methyl]cyclohexyl]-4,5-diphenyloxazole (2.23 g) and DL-methionine (7.56 g) in methanesulfonic acid (33.0 ml) was stirred at 60° C. for 17 hours, then another DL-methionine (7.56 g) and methanesulfonic acid (33.0 ml) was added thereto. The mixture was stirred at the same temperature for 23 hours and poured into ice-water. The resulting aqueous mixture was extracted three times with ethyl acetate. The extracts were combined, washed with sodium bicarbonate aqueous solution and brine, dried over magnesium sulfate, and evaporated in vacuo. The residue was chromatographed (n-hexane-diethyl ether (100:20)) over silica gel. The first eluate afforded 2-[6-[(3-hydroxyphenyl)methyl]-1-cyclohexen-1-yl]-4,5-diphenyloxazole (897 mg) as paste.

IR (Neat) : 3350, 1590 cm$^{-1}$

NMR (CDCl$_3$, δ) : 1.50–1.83 (4H, br), 2.29–2.35 (2H, br), 2.43–2.54 (1H, m), 3.12–3.34 (2H, m), 5.67 (1H, br), 6.64–6.65 (1H, m), 6.80–6.91 (3H, m), 7.12 (1H, t, J=7.7Hz), 7.31–7.40 (6H, m), 7.57–7.71 (4H, m)

Mass ((+)APCI) : 408 (M$^+$+1)

PREPARATION 10

To a solution of a mixture of 1,2-epoxycyclopentane (7.0 g) and copper(I) chloride (260 mg) in tetrahydrofuran (70 ml) was added 3-methoxyphenylmagnesium bromide (53.5 m mol) in tetrahydrofuran (60 ml) at −78° C. under N$_2$. The mixture was stirred for 1 hour at 0° C. The reaction mixture was poured into a mixture of ethyl acetate and 1N-hydrochloric acid and then the organic layer was washed with saturated sodium bicarbonate aqueous solution and brine. The combined organic extracts were concentrated and the residue was purified by column chromatography on silica gel to give 1-hydroxy-2-(3-methoxyphenyl)-cyclopentane (13 g).

IR (Neat) : 3350, 1605 cm$^{-1}$

NMR (CDCl$_3$, δ) : 1.5–2.3 (7H, m), 2.7–2.9 (1H, m), 3.80 (3H, s), 4.0–4.2 (1H, m), 6.7–6.9 (3H, m), 7.23 (1H, t, J=8Hz)

Mass : 175 (M$^+$+1 − H$_2$O)

PREPARATION 11

The following compound was obtained according to a similar manner to that of Preparation 10.

1-(Hydroxy-2-(3-methoxyphenyl)cyclohexane

IR (Neat) : 3400, 1605 cm$^{-1}$

NMR (CDCl$_3$, δ) : 1.2–2.4 (10H, m), 3.5–3.7 (1H, m), 3.80 (3H, s), 6.7–7.0 (3H, m), 7.1–7.3 (1H, m)

Mass : 189 (M$^+$+1–18)

PREPARATION 12

To a solution of oxalic chloride (9.0 ml) in methylene chloride (200 ml) was added dimethyl sulfoxide (9.6 ml) at −78° C. After 10 minutes, to the solution was added a solution of 1-hydroxy-2-(3-methoxyphenyl)cyclopentane (13 g) in methylene chloride (20 ml) at the same temperature. After 15 minutes, to the mixture was added triethylamine at −78° C. and the mixture was warmed at 0° C. for 1 hour. The reaction mixture was washed with water and brine and dried over magnesium sulfate. The organic solution was concentrated and the residue was purified by column chromatography on silica gel to give 2-(3-methoxyphenyl)cyclopentanone (8.9 g).

IR (Neat) : 1730, 1600 cm$^{-1}$

NMR (CDCl$_3$, δ) : 1.8–2.6 (6H, m), 3.29 (1H, dd, J=9.0, 11.5Hz), 3.79 (3H, s), 6.7–6.9 (3H, m), 7.24 (1H, t, J=8.0Hz)

Mass : 191 (M$^+$+1)

PREPARATION 13

The following compound was obtained according to a similar manner to that of Preparation 12.

2-(3-Methoxyphenyl)cyclohexanone

IR (Neat) : 1710 cm$^{-1}$

NMR (CDCl$_3$, δ) : 1.7–2.6 (8H, m), 3.5–3.7 (1H, m), 3.79 (3H, s), 6.6–6.9 (3H, m), 7.25 (1H, t, J=7Hz)

Mass : 205 (M$^+$+1)

PREPARATION 14

To a solution of diethyl phosphono acetic acid (8.0 ml) in 1,2-dimethoxyethane (80 ml) was added sodium hydride (60% in oil, 1.4 g) at 0° C. under N$_2$. After being stirred for 1 hour at ambient temperature, to the solution was added a solution of 2-(3-methoxyphenyl)cyclopentanone (4.5 g) in 1,2-dimethoxyethane (20 ml). After being stirred for 12 hours, the reaction mixture was poured into a mixture of ethyl acetate and water. The organic layer was washed with saturated sodium bicarbonate aqueous solution and brine. The dried solvent was concentrated and the obtained residue was purified by column chromatography on silica gel to give ethyl [2-(3-methoxyphenyl)cyclopentylidene]acetate (5.0 g).

IR (Neat) : 1700 cm$^{-1}$

NMR (CDCl$_3$, δ) : 1.26 (3H, t, J=7Hz), 1.4–2.3 (4H, m), 2.4–3.2 (3H, m), 3.80 (3H, s), 4.16 (2H, q, J=7Hz), 5.40 (1H, s), 6.6–7.0 (3H, m), 7.1–7.3 (1H, m)

Mass : 261 (M$^+$+1)

PREPARATION 15

The following compounds were obtained according to a similar manner to that of Preparation 14.

(1) Ethyl [2-(3-methoxybenzyl)cyclohexylidene]acetate

IR (Neat) : 1710, 1640, 1600 cm$^{-1}$

NMR (CDCl$_3$, δ) : 1.2–1.4 (3H, m), 1.4–2.0 (6H, m), 2.2–3.2 (5H, m), 3.79 (3H, s), 4.0–4.3 (2H, m), 5.60 (1H, s), 6.6–6.9 (3H, m), 7.0–7.3 (1H, m)

Mass : 289 (M$^+$+1)

(2) Ethyl [2-(3-methoxyphenyl)cyclohexylidene]acetate

IR (Neat) : 1700, 1630 cm$^{-1}$

NMR (CDCl$_3$, δ) : 1.22 (3H, t, J=7Hz), 1.4–2.3 (7H, m), 3.3–3.5 (1H, m), 3.6–3.8 (1H, m), 3.80 (3H, s), 5.14 (1H, s), 6.6–6.9 (3H, m), 7.25 (1H, t, J=8Hz)

Mass : 275 (M$^+$+1)

PREPARATION 16

To a solution of ethyl [2-(3-methoxyphenyl)-cyclohexylidene]acetate (1.5 g) in benzene (20 ml) was added 1,8-diazabicyclo[5.4.0]-7-undecene (1 ml) and the mixture was stirred for 3 days under reflux. And then the mixture was washed with water, 1N-hydrochloric acid, saturated sodium bicarbonate aqueous solution, and brine. The dried solvent was evaporated to give 1-(3-methoxyphenyl)-2-(ethoxycarbonylmethyl)cyclohexene (1.4 g).

IR (Neat) : 1720 cm$^{-1}$

NMR (CDCl$_3$, δ) : 1.23 (3H, t, J=7Hz), 1.5–2.4 (8H, m), 2.90 (2H, s), 3.79 (3H, s), 4.09 (2H, q, J=7Hz), 6.7–6.9 (3H, m), 7.1–7.3 (1H, m)

Mass : 275 (M$^+$+1)

PREPARATION 17

To a solution of 3-methoxybenzylmagnesium chloride (19.8 mole) in tetrahydrofuran (20 ml) was added a mixture of 2-cyclohexen-1-one (1.9 g) and trimethylsilyl chloride (5.8 ml) in tetrahydrofuran (30 ml) at −78° C. under $N_2$. The mixture was stirred for 1 hour at 0° C. The reaction mixture was poured into a mixture of ethyl acetate and 1N-hydrochloric acid and the organic layer was washed with saturated sodium bicarbonate aqueous solution and brine. The combined organic extracts were concentrated and the residue was purified by column chromatography on silica gel to give 3-(3-methoxybenzyl)cyclohexanone (2.12 g).

IR (Neat) : 1705 $cm^{-1}$

NMR ($CDCl_3$, δ) : 1.2–2.6 (11H, m), 3.80 (3H, s), 6.6–6.8 (3H, m), 7.20 (1H, t, J=8Hz)

Mass : 219 ($M^+$+1)

PREPARATION 18

The following compounds were obtained according to a similar manner to that of Preparation 17.

(1) 3-(3-Methoxyphenyl)cyclohexanone
  IR (Neat) : 1705, 1605 $cm^{-1}$
  NMR ($CDCl_3$, δ) : 1.6–2.6 (8H, m), 2.8–3.1 (1H, m), 3.81 (3H, s), 6.7–7.0 (3H, m), 7.1–7.3 (1H, m)
  Mass : 205 ($M^+$+1)

(2) 3-(3-Methoxyphenyl)cyclopentanone
  IR (Neat) : 1740 $cm^{-1}$
  NMR ($CDCl_3$, δ) : 1.8–2.8 (6H, m), 3.3–3.6 (1H, m), 3.81 (3H, s), 6.7–6.9 (3H, m), 7.2–7.4 (1H, m)
  Mass : 191 ($M^+$+1)

PREPARATION 19

The following compounds were obtained according to a similar manner to that of Preparation 1.

(1) 1-Cyano-3-(3-methoxybenzyl)cyclohexane
  IR (Neat) : 2220, 1600 $cm^{-1}$
  NMR ($CDCl_3$, δ) : 0.8–2.2 (9H, m), 2.2–2.6 (3H, m), 3.44 (3H, s), 6.6–6.8 (3H, m), 7.24 (1H, t, J=8Hz)
  Mass : 230 ($^{M+}$+1)

(2) 1-Cyano-3-(3-methoxyphenyl)cyclopentane
  IR (Neat) : 2220, 1600 $cm^{-1}$
  NMR ($CDCl_3$, δ) : 1.5–2.6 (6H, m), 2.8–3.4 (2H, m), 3.80 (3H, s), 6.7–6.9 (3H, m), 7.2–7.4 (1H, m)
  Mass : 202 ($M^+$+1)

(3) 1-Cyano-3-(3-methoxyphenyl)cyclohexane
  IR (Neat) : 2220, 1600 $cm^{-1}$
  NMR ($CDCl_3$, δ) : 1.4–2.6 (9H, m), 2.8–3.0 (1H, m), 3.80 (3H, s), 6.7–7.0 (3H, m), 7.1–7.3 (1H, m)
  Mass : 216 ($M^+$+1)

PREPARATION 20

The following compounds were obtained according to a similar manner to that of Preparation 2.

(1) 3-(3-Methoxybenzyl)cyclohexanecarboxylic acid
  IR (Neat) : 1700, 1600 $cm^{-1}$
  NMR ($CDCl_3$, δ) : 0.8–2.8 (11H, m), 3.79 (3H, s), 6.6–6.8 (3H, m), 7.18 (1H, t, J=8Hz)
  Mass : 249 ($M^+$+1)

(2) 3-(3-Methoxyphenyl)cyclopentanecarboxylic acid
  NMR ($CDCl_3$, δ) : 1.8–2.5 (6H, m), 2.9–3.3 (2H, m), 3.80 (3H, s), 6.6–7.0 (3H, m), 7.22 (1H, t, J=8Hz)
  Mass : 221 ($M^+$+1)

(3) 3-(3-Methoxyphenyl)cyclohexanecarboxylic acid
  IR (Neat) : 1690, 1600 $cm^{-1}$
  NMR ($CDCl_3$, δ) : 1.4–2.9 (10H, m), 3.79 (3H, s), 6.6–6.9 (3H, m), 7.1–7.3 (1H, m)
  Mass : 235 ($M^+$+1)

PREPARATION 21

Sodium carbonate (11.13 g) was added portionwise to a stirred solution of dihydroxy-(3-methoxyphenyl)borane (5.85 g) and 3-iodobenzoic acid (8.68 g) in water (138 ml) at room temperature, and then palladium(II) acetate (78.6 mg) was added portionwise thereto at the same temperature. The resulting mixture was stirred at the same temperature for 4 hours. The reaction mixture was filtered, then the filtrate was washed twice with diethyl ether and adjusted to pH 2.0 with 6N hydrochloric acid. The precipitated powder was collected by filtration and dissolved in ethyl acetate. The solution was dried over magnesium sulfate and evaporated in vacuo. The residue was washed with n-hexane to afford 3'-methoxy-3-biphenylcarboxylic acid (4.34 g) as a powder.

mp : 128.9–132.3° C.

IR (Nujol) : 1670 $cm^{-1}$

NMR (DMSO-$d_6$, δ) : 3.85 (3H, s), 6.97–7.01(1H, m), 7.22–7.28 (2H, m), 7.38–7.46 (1H, m), 7.56–7.64 (1H, m), 7.92–7.97 (2H, m), 8.18–8.24 (1H, m)

(−) APCI Mass : 227 ($M^+$−1)

PREPARATION 22

A suspension of 3'-methoxy-3-biphenylcarboxylic acid (4.1 g) and DL-methionine (26.7 g) in methanesulfonic acid (116 ml) was stirred at room temperature for 22 hours, diluted with water, and extracted three times with diethyl ether. The extracts were combined, washed with brine, dried over magnesium sulfate, and evaporated in vacuo. The residue was crystallized from n-hexane to afford 3'-hydroxy-3-biphenylcarboxylic acid (3.59 g) as a colorless powder.

mp 169.4–170.6° C.

IR (Nujol) : 3300, 1685 $cm^{-1}$

NMR (DMSO-$d_6$, δ) : 6.79–6.84 (1H, m), 7.06–7.13 (2H, m), 7.25–7.33 (1H, m), 7.55–7.63 (1H, m), 7.84–7.96 (2H, m), 8.12–8.14 (1H, m), 9.59 (1H, br)

(+) APCI Mass : 215 ($M^+$+1)

PREPARATION 23

The following compounds were obtained according to a similar manner to that of Preparation 3.

(1) 2-Oxo-1,2-diphenylethyl 1-cyclohexenecarboxylate
  IR (Nujol) : 1705, 1690 $cm^{-1}$
  NMR ($CDCl_3$, δ) : 1.59–1.70 (4H, m), 2.20–2.32 (4H, br m), 6.91 (1H, s), 7.14–7.18 (1H, m), 7.32–7.54 (8H, m), 7.94–7.99 (2H, m)
  (+) APCI Mass : 321 ($M^+$+1)

(2) 2-Oxo-1,2-diphenylethyl 2-bromobenzoate
  mp : 109.6–111.1° C.
  IR (Nujol) : 1725, 1692 $cm^{-1}$
  NMR ($CDCl_3$, δ) : 7.12 (1H, s), 7.33–7.50 (6H, m), 7.54–7.58 (3H, m), 7.64–7.69 (1H, m), 7.97–8.07 (3H, m)
  (+) APCI Mass : 397 ($M^+$+2), 395 ($M^+$)

PREPARATION 24

The following compounds were obtained according to a similar manner to that of Preparation 4.

(1) 2-(1-Cyclohexenyl)-4,5-diphenyloxazole
  IR (Nujol) : 1600 $cm^{-1}$
  NMR ($CDCl_3$, δ) : 1.65–1.83 (4H, m), 2.27–2.30 (2H, m), 2.54–2.58 (2H, m), 6.87–6.91 (1H, m), 7.29–7.40 (6H, m), 7.57–7.81 (4H, m)
  (+) APCI Mass : 302 ($M^+$+1)

(2) 2-(2-Bromophenyl)-4,5-diphenyloxazole mp 80.8–82.5° C.

IR (Nujol) : 1600 cm$^{-1}$

NMR (CDCl$_3$, δ) : 7.25–7.47 (8H, m), 7.70–7.78 (5H, m), 8.12 (1H, dd, J=1.8Hz, 7.7Hz)

(+) APCI Mass : 378 (M$^+$+2), 376 (M$^+$)

PREPARATION 25

N-Bromosuccinimide (2.64 g) was added to a stirred suspension of 2-(1-cyclohexenyl)-4,5-diphenyloxazole (3.00 g) in dimethyl sulfoxide (20 ml) and water (267 mg) at room temperature and the resulting mixture was stirred at the same temperature for 19 hours. The reaction mixture was partitioned between ethyl acetate and water. The organic layer was separated, washed with water and brine, dried over sodium sulfate, and evaporated in vacuo. The residue was purified by column chromatography to afford 2-bromo-1-(4,5-diphenyl-2-oxazolyl)cyclohexanol (1.52 g) as a yellow solid.

mp : 128.8–130.4° C.

IR (Nujol) : 3200, 1600 cm$^{-1}$

NMR (CDCl$_3$, δ) : 1.5–1.6 (2H, m), 1.83–2.04 (4H, m), 2.33–2.56 (3H, m), 3.64 (1H, s), 4.40 (1H, dd, J=5.5Hz, 7.3Hz), 7.29–7.43 (6H, m), 7.57–7.70 (4H, m)

(+) APCI Mass : 400 (M$^+$+2), 398 (M$^+$)

PREPARATION 26

A mixture of 2-bromo-1-(4,5-diphenyl-2-oxazolyl)-cyclohexanol (120 mg) and potassium carbonate (83 mg) in N,N-dimethylformamide (0.3 ml) was stirred at room temperature for 6 hours and partitioned between ethyl acetate and water. The organic layer was washed with brine, dried over magnesium sulfate, and evaporated in vacuo to afford 2-(1,2-epoxycyclohexyl)-4,5-diphenyloxazole (94 mg) as a pale yellow powder.

mp : 65.8–76.0° C.

IR (Neat) : 1600 cm$^{-1}$

NMR (CDCl$_3$, δ) : 1.30–1.63 (4H, m), 1.94–2.14 (2H, m), 2.28–2.42 (1H, m), 2.56–2.73 (1H, m), 3.83–3.84 (1H, m), 7.31–7.42 (6H, m), 7.52–7.66 (4H, m)

(+) APCI Mass : 318 (M$^+$+1)

PREPARATION 27

4,4'-Dimethylbenzoin (25.0 g), formamide (230 ml) and phosphorus oxychloride (16.0 ml) was mixed and stirred under reflux for 5.5 hours. The reaction mixture was cooled to room temperature and poured into water, and then extracted with diethyl ether twice. The collected organic phases were washed with brine and dried over magnesium sulfate and activated carbon. The mixture was filtered and evaporated in vacuo, and then purified by column chromatography on silica. The solvent was evaporated to afford 4,5-bis(4-methylphenyl)oxazole (15.41 g) as a solid.

mp : 93.0–94.3° C.

IR (Nujol) : 1610 cm$^{-1}$

NMR (CDCl$_3$, δ) : 2.37 (6H, s), 7.16–7.20 (4H, m), 7.47–7.51 (4H, m), 7.91 (1H, s)

(+) APCI Mass : 250 (M$^+$+1)

Analysis Calcd. for C$_{17}$H$_{15}$NO: C 81.90, H 6.06, N 5.62 Found : C 81.95, H 6.00, N 5.58

PREPARATION 28

A tetrahydrofuran (50 ml) solution of 3-methoxybenzyl chloride (14.01 g) was added slowly to a suspension of magnesium (2.18 g) and iodine (a catalytic amount) in tetrahydrofuran (50 ml) at 60° C. over 40 minutes. After 1 hour stirring at the same temperature, the reaction mixture was cooled to the room temperature. An insoluble material was filtered off and the Grignard solution was prepared. The Grignard solution was added slowly to a suspension of ethyl 5(R)-acetoxy-1-cyclopentenecarboxylate (4.50 g) and copper(I) iodide (0.56 g) in tetrahydrofuran (100 ml) over 1 hour at −60° C. After 1 hour stirring at the same temperature, 1N-hydrochloric acid (100 ml) was added to the reaction mixture. The mixture was extracted with ethyl acetate The extract was washed with 1N-hydrochloric acid, water, saturated aqueous sodium hydrogencarbonate and brine. Drying (sodium sulfate) and removal of solvent at reduced pressure followed by flash chromatography over 250 g of silica afforded (−)-ethyl 5(S)-(3-methoxybenzyl)-1-cyclopentencarboxylate as a colorless oil (4.73 g).

[α]$_D$: −11.2° (C=1, CH$_2$Cl$_2$)

IR (Film) : 1700, 1620 cm$^{-1}$

NMR (CDCl$_3$, δ) : 1.31 (3H, t, J=7.0Hz), 1.74–2.04 (2H, m), 2.32–2.46 (3H, m), 3.09–3.23 (2H, m), 3.80 (3H, s), 4.21 (2H, q, J=7.0Hz), 6.72–6.80 (4H, m), 7.15–7.26 (1H, m)

Mass (APCI) m/e : 261 (M$^+$+1)

PREPARATION 29

The following compound was obtained according to a similar manner to that of Preparation 28.

(+)-Ethyl 5(R)-(3-methoxybenzyl)-1-cyclopentenecarboxylate

[α]$_D$:+11.8° (C=1.05, CH$_2$Cl$_2$)

IR (Film) : 1700, 1620 cm$^{-1}$

NMR (CDCl$_3$, δ) : 1.31 (3H, t, J=7.0Hz), 1.74–2.04 (2H, m), 2.32–2.46 (3H, m), 3.09–3.23 (2H, m), 3.80 (3H, s), 4.21 (2H, q, J=7.0Hz), 6.72–6.80 (4H, m), 7.15–7.26 (1H, m)

Mass (APCI) m/e : 261 (M$^+$+1)

PREPARATION 30

To a solution of sodium hydride (1.0 g, 60% in oil) in N,N-dimethylformamide (50 ml) was added trimethylsulfonium iodide (6.1 g) at ambient temperature under N$_2$ and stirred for 20 minutes. To the solution was added dropwise a solution of trans-1-ethoxycarbonyl-2-(3-methoxyphenyl)ethylene (5.2 g) in N,N-dimethylformamide (10 ml) and stirred for 2 hours. The reaction mixture was poured into a mixture of ethyl acetate (100 ml) and 1N-hydrochloric acid (100 ml). The organic layer was washed with water, saturated sodium bicarbonate aqueous solution, and brine, and then dried over magnesium sulfate. The solution was evaporated and the residue was chromatographed (hexane:ethyl acetate=4:1) to give trans-1-ethoxycarbonyl-2-(3-methoxyphenyl)cyclopropane (1.0 g).

IR (Neat) : 1720 cm$^{-1}$

NMR (CDCl$_3$, δ) : 0.7–0.9 (1H, m), 1.25 (3H, t, J=7.0Hz), 1.5–1.7 (1H, m), 1.8–2.0 (1H, m), 2.4–2.6 (1H, m), 3.78 (3H, s), 4.16 (2H, q; J=7.0Hz), 6.6–6.9 (3H, m), 7.19 (1H, t, J=8.0Hz)

Mass : 221 (M$^+$+1)

PREPARATION 31

An ethanol (30 ml) solution of (−)-ethyl 5(S)-(3-methoxybenzyl)-1-cyclopentencarboxylate (4.30 g) and 1N aqueous sodium hydroxide solution (25 ml) was stirred at 60° C. for 4 hours. The solvent was removed in vacuo and the residue was partitioned between diethyl ether and water. The aqueous layer was acidified with 1N hydrochloric acid and extracted with ethyl acetate. The extract was washed with brine and dried over sodium sulfate. Removal of solvent afforded a crude carboxylic acid as a yellow oil (3.82 g, [α]$_D$: −9.65° (C=1, CH$_2$Cl$_2$)).

To a n-hexane and ethyl acetate solution (80 ml, 1:1) of the crude carboxylic acid was added (+)-1-phenylethylamine (1.96 g) with stirring at the room temperature. A precipitated colorless powder (3.97 g, mp : 125–131° C.) was collected by filtration and the additional powder (0.20 g, mp : 127–129° C.) was obtained from the filtrate Recrystallization of the combined powder from n-hexane—ethyl acetate (1:1, 100 ml) afforded a pure salt of (−)-5(S)-(3-methoxybenzyl)-1-cyclopentenecarboxylic acid and (+)-1-phenylethylamine as a colorless needles (3.27 g, mp : 135–136° C., [α]$_D$: −21.87° (C=1, MeOH)).

The salt was portioned between ethyl acetate and 1N-hydrochloric acid. The organic layer was washed with 1N-hydrochloric acid and brine. Drying (sodium sulfate) and removal of the solvent afforded (−)-5(S)-(3-methoxybenzyl)-1-cyclopentenecarboxylic acid as a colorless oil (2.09 g).

[α]$_D$: −14.91° (C=1.2, CH$_2$Cl$_2$)

IR (Film) : 1700, 1665 cm$^{-1}$

NMR (CDCl$_3$, δ) : 1.74–2.12 (2H, m), 2.36–2.49 (3H, m), 3.15–3.23 (2H, m), 3.81 (3H, s), 6.73–6.83 (3H, m), 6.97 (1H, m), 7.16–7.26 (1H, m)

Mass (APCI) m/e 233 (M$^+$+1)

PREPARATION 32

The following compounds were obtained according to a similar manner to that of Preparation 31.

(1) (+)-5(R)-(3-Methoxybenzyl)-1-cyclopentenecarboxylic acid
[α]$_D$: +15.09° (C=1.04, CH$_2$Cl$_2$)
IR (Film) : 1700, 1665 cm$^{-1}$
NMR (CDCl$_3$,δ) : 1.74–2.12 (2H, m), 2.36–2.49 (3H, m), 3.15–3.23 (2H, m), 3.81 (3H, s), 6.73–6.83 (3H, m), 6.97 (1H, m), 7.16–7.26 (1H, m)
Mass (APCI) m/e : 233 (M$^+$+1)

(2) trans-2-(3-Methoxyphenyl)cyclopropanecarboxylic acid
NMR (CDCl$_3$, δ) : 1.3–1.5 (1H, m), 1.6–1.8 (1H, m), 1.8–2.0 (1H, m), 2.5–2.7 (1H, m), 3.79 (3H, s), 6.6–6.9 (3H, m), 7.20 (1H, t, J=8.0Hz)
FAB Mass : 192 (M$^+$+1)

(3) [2-(3-Methoxyphenyl)cyclopentylidene]acetic acid
Mass : 233 (M$^+$+1)

(4) [2-(3-Methoxyphenyl)cyclohexylidene]acetic acid
IR (Nujol) : 1700, 1640 cm$^{-1}$
NMR (CDCl$_3$, δ) : 1.4–2.4 (7H, m), 3.3–3.5 (1H, m), 3.6–3.8 (1H, m), 3.78 (3H, s), 5.17 (1H, s)
Mass : 247 (M$^+$+1)

(5) [1-(3-Methoxyphenyl)cyclohexen-2-yl]acetic acid
IR (Nujol) : 1700 cm$^{-1}$
NMR (CDCl$_3$, δ) : 1.5–2.4 (8H, m), 2.98 (2H, s), 3.79 (3H, s), 6.6–6.8 (3H, m), 7.1–7.3 (1H, m)
Mass : 247 (M$^+$+1)

(6) [2-(3-Methoxybenzyl)cyclohexylidene]acetic acid
IR (Neat) : 1680, 1630, 1600 cm$^{-1}$
NMR (CDCl$_3$, δ) : 1.3–1.9 (6H, m), 2.2–3.2 (5H, m), 3.79 (3H, s), 5.62 (1H, s), 6.6–6.8 (3H, m), 7.0–7.3 (1H, m)
Mass : 261 (M$^+$+1)

PREPARATION 33

The following compound was obtained according to a similar manner to that of Preparation 3.

2-Oxo-1,2-bis(4-methylphenyl)ethyl 2-(3-methoxyphenylmethyl)cyclohexanecarboxylate IR (Neat) : 1725, 1685 cm$^{-1}$ NMR (CDCl$_3$, δ) : 1.16–2.00 (8H, br m), 2.0–2.3 (1H, m), 2.31 (3H, s), 2.34 (3H, s), 2.43 (1H, m), 2.57–2.92 (2H, m), 3.69–3.80 (3H, m), 6.58–6.76 (2H, m), 6.83–6.91 (1H, m), 7.05–7.25 (6H, m), 7.27–7.38 (2H, m), 7.82–7.87 (2H, m)

(+) APCI Mass : 471 (M$^+$+1)

PREPARATION 34

Sodium (64 mg) was dissolved in ethanol (10 ml) and 3'-hydroxy-3-biphenylcarboxylic acid (0.5 g) was added thereto. The mixture was stirred at room temperature for 20 minutes, and then conc. sulfuric acid (1 drop) and desyl bromide (642 mg) was added thereto. The resulting mixture was stirred under reflux for 3 hours, cooled to room temperature, and partitioned between water and ethyl acetate. The organic layer was washed successively with water (twice), 1N hydrochloric acid, sodium bicarbonate aqueous solution, and brine, dried over magnesium sulfate, and evaporated in vacuo. The residue was chromatographed (n-hexane—ethyl acetate) over silica gel to afford 2-oxo-1, 2-diphenylethyl 3'-hydroxy-3-biphenylcarboxylate (744 mg) as a paste.

IR (Neat) : 3370, 1720, 1690 cm$^{-1}$

NMR (CDCl$_3$, δ) : 5.75 (1H, br), 6.82–6.86 (1H, m), 7.05–7.13 (3H, m), 7.23–7.27 (1H, m), 7.37–7.60 (9H, m), 7.71 (1H, m), 7.99–8.10 (3H, m), 8.29–8.30 (1H, m)

Mass ((+)APCI) : 409 (M$^+$+1)

PREPARATION 35

The following compounds were obtained according to a similar manner to that of Preparation 4.

(1) 2-[2-(3-Methoxyphenylmethyl)cyclohexyl]-4,5-bis(4-methylphenyl)oxazole
IR (Neat) : 1590 cm$^{-1}$
NMR (CDCl$_3$, δ) : 1.3–1.8 (12H, br m), 2.04–2.09 (4H, br m), 2.28–2.32 (2H, m), 2.37 (12H, s), 2.51–2.78 (4H, m), 3.20 (2H, m), 3.70 (3H, s), 3.71 (3H, s), 6.64–6.72 (6H, m), 7.07–7.18 (10H, m), 7.43–7.59 (8H, m)
(+) APCI Mass : 452 (M$^+$+1)

(2) 2-(31-Hydroxy-3-biphenylyl)-4,5-diphenyloxazole
IR (Neat) : 3350, 1600 cm$^{-1}$
NMR (DMSO-d$_6$, δ) : 6.82–6.87 (1H, m), 7.14–7.20 (2H, m), 7.29–7.33 (1H, m), 7.42–7.53 (6H, m), 7.62–7.73 (5H, m), 7.79–7.83 (1H, m), 8.08–8.12 (1H, m), 8.28 (1H, m), 9.64 (1H, s)
Mass ((+)APCI) : 390 (M$^+$+1)

PREPARATION 36

A methylene chloride solution (20 ml) of (−)-5(S)-(3-methoxybenzyl)- 1-cyclopentenecarboxylic acid (1.99 g), thionyl chloride (2 ml) and N,N-dimethylformamide (2 drops) was stirred for 3 hours at room temperature. Removal of solvent at reduced pressure afforded the crude acid chloride as a brown oil. To a methylene chloride solution (20 ml) of the crude acid chloride and benzoin (1.97 g), pyridine (2 ml) was added at room temperature. The solution was stirred for 4 hours at the same temperature and washed with IN hydrochloric acid (×2) and brine. Drying (sodium sulfate) and removal of solvent afforded a yellow oil. An acetic acid solution (80 ml) of the yellow oil and ammonium acetate (14.98 g) was stirred for 7.5 hours at 130° C. and cooled to room temperature. Solvent was removed and the residue was dissolved in ethyl acetate. The solution was washed with water, saturated aqueous sodium hydrogen carbonate (×3), water, and brine. Drying (sodium sulfate) and removal of solvent at reduced pressure followed by flash chromatography on 100 g of silica afforded (+)-1-(4,5-diphenyloxazol-2-yl)-5(S)-(3-methoxybenzyl)cyclopentene as a pale yellow solid (2.69 g, 99.6% ee).

mp : 73–75° C.

$[\alpha]_D$:+65.24° (C=1.075, $CH_2Cl_2$)

IR (Nujol) : 1600 $cm^{-1}$

NMR ($CDCl_3$, δ) : 1.89 (1H, m), 2.00–2.11 (1H, m), 2.46 (2H, m), 2.62 (1H, dd, J=13.3Hz, 9.6Hz), 3.41 (1H, dd, J=13.3Hz, 4.1Hz), 3.56 (1H, m), 3.77 (3H, s), 6.70–6.87 (4H, m), 7.15–7.72 (11H, m)

Mass (APCI) m/e : 408 ($M^+$+1)

PREPARATION 37

The following compound was obtained according to a similar manner to that of Preparation 36.

(−)-1-(4,5-Diphenyloxazol-2-yl)-5(R)-(3-methoxybenzyl)cyclopentene $[\alpha]_D$: −46.91° (C=1.29, $CH_2Cl_2$)
IR (Film) : 1600 $cm^{-1}$
NMR ($CDCl_3$, δ) : 1.89 (1H, m), 2.00–2.11 (1H, m), 2.46 (2H, m), 2.62 (1H, dd, J=13.3Hz, 9.6Hz), 3.41 (1H, dd, J=13.3Hz, 4.1Hz), 3.56 (1H, m), 3.77 (3H, s), 6.70–6.87 (4H, m), 7.15–7.72 (11H, m)
Mass (APCI) m/e : 408 ($M^+$+1)

PREPARATION 38

The following compounds were obtained according to similar manners to those of Preparations 3 and 4.

(1) 1-(4,5-Diphenyloxazol-2-yl)-2-(3-methoxyphenyl)cyclopropane
IR (Neat) : 1610, 1590 $cm^{-1}$
NMR ($CDCl_3$, δ) : 1.4–1.6 (1H, m), 1.7–1.9 (1H, m), 2.3–2.5 (1H, m), 2.6–2.8 (1H, m), 3.74 (3H, s), 6.7–7.9 (3H, m), 7.2–7.8 (11H, s)
Mass : 368 ($M^+$+1)

(2) 2-[(4,5-Diphenyloxazol-2-yl)methylene]-1-(3-methoxyphenyl)cyclohexane
IR (Neat) : 1640 $cm^{-1}$
NMR ($CDCl_3$, δ) : 1.4–2.4 (7H, m), 3.4–3.6 (1H, m), 3.81 (3H, s), 3.7–3.9 (1H, m), 5.66 (1H, s), 6.7–6.9 (3H, m), 7.2–7.8 (11H, m)
Mass : 422 ($M^+$+1)

(3) 1-(3-Methoxyphenyl)-2-[(4,5-diphenyloxazol-2-yl)methyl]cyclohexene
IR (Neat) : 1600 $cm^{-1}$
NMR ($CDCl_3$, δ) : 1.6–1.8 (4H, m), 2.1–2.4 (4H, m), 3.48 (2H, s), 3.76 (3H, s), 6.7–6.9 (3H, m), 7.2–7.8 (11H, m)
Mass : 422 ($M^+$+1)

(4) 2-[[2-(3-Methoxybenzyl)cyclohexylidene]methyl]-4,5-diphenyloxazole
IR (Neat) : 1640, 1610 $cm^{-1}$
NMR ($CDCl_3$, δ) : 1.2–1.9 (6H, m), 2.4–3.3 (5H, m), 3.80 (3H, s), 6.13 (1H, s), 6.6–6.9 (3H, m), 7.0–7.8 (11H, m)
Mass : 436 ($M^+$+1)

(5) 1-(4,5-Diphenyloxazol-2-yl)-3-(3-methoxybenzyl)cyclohexane
IR (Neat) : 1600, 1590 $cm^{-1}$
NMR ($CDCl_3$, δ) : 0.8–2.2 (9H, m), 2.5–2.7 (2H, m), 2.8–3.3 (1H, m), 3.76, 3.80 (3H, each s), 6.7–6.9 (3H, m), 7.1–7.8 (11H, m)
Mass : 424 ($M^+$+1)

(6) 1-(4,5-Diphenyloxazol-2-yl)-3-(3-methoxyphenyl)cyclopentane
IR (Neat) : 1600 $cm^{-1}$
NMR ($CDCl_3$, δ) : 1.8–2.6 (6H, m), 3.0–3.8 (2H, m), 3.79, 3.81 (3H, each s), 6.6–7.0 (3H, m), 7.0–7.8 (11H, m)
Mass : 396 ($M^+$+1)

(7) 1-(4,5-Diphenyloxazol-2-yl)-3-(3-methoxyphenyl)cyclohexane
IR (Neat) : 1600 $cm^{-1}$
NMR ($CDCl_3$, δ) : 1.4–2.9 (9H, m), 2.9–3.1 (1H, m), 3.80 (3H, s), 6.6–7.0 (3H, m), 7.2–7.8 (11H, m)
Mass : 410 ($M^+$+1)

PREPARATION 39

To a solution of [2-(3-methoxyphenyl)-cyclopentylidene]acetic acid (4.0 g) in methylene chloride (80 ml) were added benzoin (3.7 g), 1-ethyl-3-(3-dimethylaminopropyl)carbodimide (4.1 ml) and 4-dimethylaminopyridine (2.1 g). The resulting mixture was stirred at room temperature for 12 hours and then partitioned between ethyl acetate and 1N-hydrochloric acid. The organic layer was separated, washed successively with 1N-hydrochloric acid, saturated sodium bicarbonate aqueous solution, and brine, dried over magnesium sulfate, and evaporated in vacuo. The residue and ammonium acetate (6.6 g) were dissolved in acetic acid (40 ml) and refluxed for 4 hours. The reaction mixture was evaporated in vacuo and the residue was partitioned between ethyl acetate and water. The organic layer was washed with saturated sodium bicarbonate aqueous solution and brine, dried over magnesium sulfate, and evaporated in vacuo. The residue was chromatographed by silica gel to give 2-[(4,5-diphenyloxazol-2-yl)methyl]-1-(3-methoxyphenyl)cyclopentene (4.1 g).

IR (Neat) : 1600 $cm^{-1}$
NMR ($CDCl_3$, δ) : 1.8–2.1 (2H, m), 2.6–2.9 (4H, m), 3.80 (3H, s), 3.7–3.85 (2H, m), 6.7–7.0 (3H, m), 7.2–7.8 (11H, m)
Mass : 408 ($M^+$+1)

PREPARATION 40

4,5-Bis(4-methylphenyl)oxazole (3.91 g) was dissolved in tetrahydrofuran (26 ml) and diethyl ether (13 ml) under $N_2$ gas at −75° C. 1.5N Lithium diisopropylamide was added to the solution. After 45 minutes, 2-(3-methoxyphenylmethyl)cyclopentanone was added to the reaction mixture and then stirred at room temperature for 105 minutes. The ammonium chloride aqueous solution was added to the reaction mixture and extracted with ethyl acetate. The organic layer was washed with 1N hydrochloric acid, saturated sodium bicarbonate aqueous solution and brine. The organic layer was dried on magnesium sulfate and evaporated to afford the yellow oil. The oil was purified with $SiO_2$ to afford a mixture (4.83 g) of cis- or trans-2-[1-hydroxy-2-(3-methoxyphenylmethyl)cyclopentyl]-4,5-bis (4-methylphenyl)oxazole (isomer E) and trans- or cis-2-[1-hydroxy-2-(3-methoxyphenylmethyl)cyclopentyl]-4,5-bis (4-methylphenyl)oxazole (isomer F).
isomer E
IR (Neat) : 3400, 1590 $cm^{-1}$
NMR ($CDCl_3$, δ) : 1.6–2.1 (6H, m), 2.37 (6H, s), 2.6–2.9 (3H, m), 3.26 (1H, s), 3.61 (3H, s), 6.53–6.58 (1H, m), 6.64–6.78 (2H, m), 6.94–7.07 (1H, m), 7.12–7.18 (4H, m), 7.34–7.48 (4H, m)

(+) APCI Mass : 454 (M$^+$+1)

isomer F

IR (Neat) : 3400, 1595 cm$^{-1}$

NMR (CDCl$_3$, δ) : 1.7–2.2 (6H, m), 2.38 (6H, s), 2.43–2.78 (3H, m), 3.34 (1H, s), 3.72 (3H, s), 6.66–6.73 (3H, m), 7.10–7.26 (5H, m), 7.45–7.57 (4H, m)

(+) APCI Mass : 454 (M$^+$+1)

Isomer E is different from isomer F in configuration.

PREPARATION 41

The following two compounds were obtained according to a similar manner to that of Preparation 7.

cis-2-[1-Hydroxy-2-(3-methoxybenzyl)cyclohexyl]-4,5-bis(4-methylphenyl)oxazole

IR (Neat) : 3450, 1600 cm$^{-1}$

NMR (CDCl$_3$, δ) : 1.2–1.95 (8H, br m), 2.22–2.32 (1H, m), 2.38 (6H, s), 2.42–2.69 (2H, m), 3.27 (1H, s), 3.64 (3H, s), 6.60–6.76 (3H, m), 7.03–7.19 (5H, m), 7.40–7.55 (4H, m)

(+) APCI Mass : 468 (M$^+$+1)

trans-2-[1-Hydroxy-2-(3-methoxybenzyl)cyclohexyl]-4,5-bis(4-methylphenyl)oxazole IR (Neat) : 3420, 1590 cm$^{-1}$ NMR (CDCl$_3$, δ) : 1.39–1.88 (7H, br m), 2.04–2.24 (3H, m), 2.39 (6H, s), 3.05–3.10 (1H, m), 3.58 (1H, s), 3.75 (3H, s), 6.69–6.76 (3H, m), 7.02–7.25 (5H, m), 7.48–7.60 (4H, m)

(+) APCI Mass : 468 (M$^+$+1)

PREPARATION 42

To a solution of (R,R)-mono(2,6-dimethoxybenzoyl) tartaric acid (314 mg) in propionitrile (5 ml) was added 1M BH$_3$ solution (1.0 ml) in tetrahydrofuran at 0° C. under N$_2$. The reaction mixture was stirred for 1 hour at 0° C., and then the solution was cooled to −78° C. To this were added 1-(trimethylsilyl-oxy)cyclohexene (1.0 g) and 3-methoxybenzaldehyde (680 mg) successively. After stirring for 2 hours, the solution was poured into 1N-hydrochloric acid and the product was extracted with ether. The solvent was evaporated, and the residue was treated with 1N-hydrochloric acid-tetrahydrofuran solution (2 ml, 1:1). Usual chromatographic separation gave (2R)-2-[(1-hydroxy-1-(3-methoxyphenyl)methyl]cyclohexanone (350 mg).

NMR (CDCl$_3$, δ) : 1.4–2.6 (9H, m), 3.81 (3H, s), 5.32 (1H, m), 6.6–7.4 (4H, m).

HPLC (chiralcel AD, 10% isopropanol/hexane, 1 ml/min); rt=11.2 min

PREPARATION 43

The following compound was obtained by using (S,S)-mono(2,6-dimethoxybenzoyl)tartaric acid instead of (R,R)-mono(2,6-dimethoxybenzoyl)tartaric acid in a similar manner to that of Preparation 42.

(2S)-2-[1-Hydroxy-1-(3-methoxyphenyl)methyl]cyclohexanone

HPLC (chiralcel AD, 10% isopropanol/hexane, 1 ml/min); rt13.0 min

PREPARATION 44

To a solution of (2S)-2-[1-hydroxy-1-(3-methoxyphenyl)methyl]cyclohexanone (0.8 g) in ethanol (20 ml) was added paradium on carbon (0.5 g). After being stirred for 4 hours under hydrogen atmosphere, the reaction mixture was filtered. The solvent was evaporated to give (2S)-2-(3-methoxybenzyl)cyclohexanone (0.8 g).

HPLC (chiralcel OJ, 5% isopropanol/hexane, 1 ml/min); rt=13.9 min

PREPARATION 45

The following compound was obtained according to a similar manner to that of Preparation 44.

(2R)-2-(3-Methoxybenzyl)cyclohexanone

HPLC (chiralcel OJ, 5% isopropanol/hexane, 1 ml/min); rt=11.2 min

PREPARATION 46

The following compounds were obtained according to similar manners to those of Preparations 6 and 8.

(1) (6R)-1-(4,5-Diphenyloxazol-2-yl)-6-(3-methoxybenzyl)cyclohexene

HPLC (chiralcel AD, 5% isopropanol/hexane, 1 ml/min); rt=15.5 min

IR (Neat) : 1600 cm$^{-1}$

NMR (CDCl$_3$, δ) : 1.4–2.0 (4H, m), 2.0–2.5 (3H, m), 3.0–3.4 (2H, m), 3.75 (3H, s), 6.6–6.8 (1H, m), 6.8–7.0 (3H, m), 7.0–7.8 (11H, m)

Mass : 422 (M$^+$+1)

(2) (6S)-1-(4,5-Diphenyloxazol-2-yl)-6-(3-methoxybenzyl)cyclohexene

HPLC (chiralcel AD, 5% isopropanol/hexane, 1 ml/min); rt=14.8 min

PREPARATION 47

3-Methoxybenzylmagnesium chloride was prepared from 3-methoxybenzyl chloride (1.72 g), magnesium (turnings, 243 mg), and a slight amount of iodine in tetrahydrofuran (10 ml) at room temperature −50° C. in a usual manner, and then copper(II) bromide (143 mg) was added thereto at −78° C. The Grignard reagents in tetrahydrofuran (4.0 ml) was added to a solution of 2-(1,2-epoxycyclohexyl)-4,5-diphenyloxazole (640 mg) in tetrahydrofuran (2 ml) with stirring at −78° C. The resulting mixture was stirred under ice cooling for 1 hour and 30 minutes and the additional Grignard reagents in tetrahydrofuran (3.0 ml) was added thereto at the same temperature. The mixture was stirred at room temperature overnight. The reaction mixture was treated with ammonium chloride aqueous solution and partitioned between ethyl acetate and 1N hydrochloric acid. The ethyl acetate layer was washed successively with 1N-hydrochloric acid, sodium bicarbonate aqueous solution, and brine, dried over magnesium sulfate, and evaporated in vacuo. The residue was chromatographed (n-hexane—ethyl acetate) over silica gel to afford 2-[trans-1-hydroxy-2-(3-methoxybenzyl)cyclohexyl]-4,5-diphenyloxazole (594 mg) as a paste.

IR (Neat) : 3400, 1600 cm$^{-1}$

NMR (CDCl$_3$, δ) : 1.5–1.9 (6H, br m), 2.1–2.26 (2H, m), 3.05–3.11 (1H, br m), 3.56 (1H, s), 3.75 (3H, s), 6.69–6.76 (3H, m), 7.11–7.20 (1H, m), 7.33–7.44 (6H, m), 7.58–7.72 (4H, m)

(+) APCI Mass : 440 (M$^+$+1)

PREPARATION 48

The following compound was obtained according to a similar manner to that of Preparation 47.

2-[trans-1-Hydroxy-2-(3-methoxyphenyl)cyclohexyl]-4,5-diphenyloxazole

IR (Neat) : 3350, 1590 cm$^{-1}$

NMR (CDCl$_3$, δ) : 1.5–1.6 (1H, br), 1.86–2.04 (4H, br m), 2.17–2.48 (3H, br m), 2.92–3.00 (1H, m), 3.39 (1H, s), 3.61 (3H, s), 6.4–6.7 (3H, m), 7.07–7.16 (1H, m), 7.31–7.40 (6H, m), 7.49–7.70 (4H, m)

(+) APCI Mass : 426 (M$^+$+1)

PREPARATION 49

A solution of 2-(2-bromophenyl)-4,5-diphenyloxazole (3.0 g) in tetrahydrofuran (15 ml) was added dropwise to a stirred mixture of magnesium (213 mg) and a slight amount of iodine in tetrahydrofuran (15 ml) at room temperature under a nitrogen atmosphere and the resulting mixture was stirred at 70° C. for 3 hours. The reaction mixture was added slowly to a solution of 3-benzyloxybenzaldehyde (1.69 g) in tetrahydrofuran (6 ml) under dry ice-acetone cooling and a nitrogen atmosphere. The resulting mixture was stirred at the same temperature for 3 hours and at room temperature overnight, treated with ammonium chloride aqueous solution, and partitioned between ethyl acetate and 0.5N hydrochloric acid. The organic layer was washed with sodium bicarbonate aqueous solution and brine, dried over magnesium sulfate, and evaporated in vacuo. The residue was chromatographed (n-hexane - ethyl acetate) over silica gel to afford 2-(4,5-diphenyl-2-oxazolyl)-3'-benzyloxybenzhydrol (2.21 g) as paste.

IR (Neat) : 3300, 1590 cm$^{-1}$

NMR (CDCl$_3$, δ) : 4.95–4.98 (2H, m), 6.24 (1H, br m), 6.85–6.94 (2H, m), 7.16–7.52 (16H, m), 7.64–7.69 (4H, m), 8.08–8.13 (1H, m)

(+) APCI Mass : 510 (M$^+$+1)

PREPARATION 50

A mixture of trans-1-(4,5-diphenyl-2-oxazolyl)-2-(3-methoxybenzyl)cyclohexanol (580 mg) and DL-methionine (1.97 g) in methanesulfonic acid (8.1 ml) was stirred at room temperature for 15 hours. After addition of DL-methionine (1.97 g) and methanesulfonic acid (8.1 ml), the resulting mixture was stirred at 50° C. for 5 hours and partitioned between ethyl acetate and water. The organic layer was washed successively with water (twice), sodium bicarbonate aqueous solution, and brine, dried over magnesium sulfate, and evaporated in vacuo. The residue was chromatographed (n-hexane - ethyl acetate) over silica gel to afford trans-1-(4,5-diphenyl-2-oxazolyl)-2-(3-hydroxybenzyl)cyclohexanol (357 mg) as an amorphous powder.

IR (Neat) : 3300, 1590 cm$^{-1}$

NMR (CDCl$_3$, δ) : 1.3–1.9 (8H, br m), 2.07–2.26 (2H, m), 3.02–3.07 (1H, m), 3.54 (1H, br), 6.62–6.74 (3H, m), 7.06–7.14 (1H, m), 7.35–7.45 (6H, m), 7.58–7.72 (4H, m)

(+) APCI Mass : 426 (M$^+$+1)

PREPARATION 51

The following compounds were obtained according to a similar manner to that of Preparation 50.

(1) trans-2-[1-Hydroxy-2-(3-hydroxyphenyl)cyclohexyl]-4,5-diphenyloxazole

IR (Neat) : 3350, 1600 cm$^{-1}$

NMR (CDCl$_3$, δ) : 1.50 (2H, br m), 1.86–2.04 (4H, br m), 2.15–2.35 (2H, br m), 2.88 (1H, dd, J=13.1Hz, 3.5Hz), 3.54 (1H, s), 5.48 (1H, br), 6.40–6.49 (3H, m), 6.92–7.25 (1H, m), 7.31–7.40 (6H, m), 7.50–7.58 (4H, m)

(+) APCI Mass : 412 (M$^+$+1)

(2) cis-2-[1-Hydroxy-2-(3-hydroxyphenylmethyl)-cyclohexyl]-4,5-diphenyloxazole

IR (Nujol) : 3420, 1600 cm$^{-1}$

NMR (CDCl$_3$, δ) : 1.2–1.9 (8H, br), 2.29–2.65 (3H, m), 3.58 (1H, s), 5.33 (1H, br), 6.49–6.66 (3H, m), 6.97–7.04 (1H, m), 7.26–7.42 (6H, m), 7.46–7.51 (2H, m), 7.59–7.65 (2H, m)

(+) APCI Mass : 426 (M$^+$+1)

PREPARATION 52

The following compound was obtained according to a similar manner to that of Preparation 5.

2-[2-(3-Hydroxyphenylmethyl)cyclohexyl]-4,5-bis(4-methylphenyl)oxazole

IR (Neat) : 3300, 1595 cm$^{-1}$

NMR (CDCl$_3$, δ) : 1.3–2.3 (8H, br m), 2.37 (6H, s), 2.4–3.2 (4H, br m), 6.57–6.67 (3H, m), 6.99–7.17 (5H, m), 7.30–7.60 (4H, m)

(+) APCI Mass : 438 (M$^+$+1)

PREPARATION 53

The following compounds were obtained according to a similar manner to that of Preparation 9.

(1) 2-[6-(3-Hydroxyphenylmethyl)-1-cyclohexen-1-yl]-4,5-bis(4-methylphenyl)oxazole IR (Neat) : 3450, 1600 cm$^{-1}$ NMR (CDCl$_3$, δ) : 1.38–1.84 (4H, br m), 2.27 (2H, br), 2.36 (6H, s), 2.42–2.53 (1H, br m), 3.11–3.26 (2H, br m), 5.69 (1H, br), 6.65 (1H, dd, J=2.4Hz, 7.9Hz), 6.80–6.90 (3H, br m), 7.08–7.25 (5H, br m), 7.47–7.59 (4H, br m)

(+) APCI Mass : 468 (M$^+$+1)

(2) 2-[5-(3-Hydroxyphenylmethyl)-1-cyclopenten-1-yl]-4,5-bis(4-methylphenyl)oxazole IR (Neat) : 3200, 1595 cm$^{-1}$ NMR (CDCl$_3$, δ) : 1.76–1.84 (1H, m), 1.87–2.04 (1H, m), 2.36 (6H, s), 2.40–2.68 (3H, br m), 3.30 (1H, dd, J=13.4Hz, 3.9Hz), 3.52 (1H, br), 5.90 (1H, s), 6.58–6.80 (4H, m), 7.06–7.25 (5H, m), 7.46–7.57 (4H, m)

(+) APCI Mass : 422 (M$^+$+1)

PREPARATION 54

A solution of 2-(4,5-diphenyl-2-oxazolyl)-3'-benzyloxybenzhydrol (650 mg) in ethyl acetate (3 ml), methanol (3 ml), and 10% hydrogen chloride in methanol (0.3 ml) was stirred in the presence of 10% palladium on carbon—water (50/50 wt. %) (400 mg) and hydrogen at atmospheric pressure at room temperature for 10 hours. The reaction mixture was filtered and the filtrate was evaporated in vacuo. The residue was chromatographed (toluene—ethyl acetate) over silica gel to afford 3-[[2-(4,5-diphenyl-2-oxazolyl)phenyl]methyl]phenol (150 mg) as a colorless powder.

mp : 180.7–183.0° C.

IR (Nujol) : 3150, 1600 cm$^{-1}$

NMR (CDCl$_3$, δ) : 4.57 (2H, s), 6.63–6.67 (2H, m), 6.77–6.81 (1H, m), 7.09–7.18 (1H, m), 7.26–7.42 (9H, m), 7.54–7.60 (2H, m), 7.68–7.73 (2H, m), 8.09–8.14 (1H, m)

(+) APCI Mass : 404 (M$^+$+1)

EXAMPLE 1

A mixture of 2-[2-[(3-hydroxyphenyl)methyl]-cyclohexyl]-4,5-diphenyloxazole (320 mg), ethyl bromoacetate (0.13 ml), and potassium carbonate (270 mg) in acetonitrile (3.0 ml) was stirred at room temperature overnight and a mixture of ethyl acetate and water was added thereto. The organic layer was separated, washed with water (twice) and brine, dried over magnesium sulfate, and evaporated in vacuo. The oily residue was chromatographed over silica gel using n-hexane—ethyl acetate as an eluent. The first eluate gave cis- or trans-1-[(3-ethoxycarbonylmethoxyphenyl)methyl]-2-(4,5-diphenyloxazol-2-yl)cyclohexane (isomer A) (79 mg) as a powder.

IR (Film) : 1755, 1600 cm$^{-1}$

NMR (CDCl$_3$, δ) : 1.27 (3H, t, J=7.1Hz), 1.3–1.6 (3H, m), 1.7–2.15 (5H, m), 2.31 (1H, m), 2.5–2.7 (2H, m), 3.21 (1H, m), 4.23 (2H, q, J=7.1Hz), 4.52 (2H, s), 6.6–6.8 (3H, m), 7.15 (1H, t, J=7.6Hz), 7.2–7.4 (6H, m), 7.5–7.6 (2H, m), 7.6–7.7 (2H, m)

(+) APCI Mass (m$^+$/z) : 496 (M$^+$+1)

The second eluate gave trans- or cis-1-[(3-ethoxycarbonylmethoxyphenyl)methyl]-2-(4,5-diphenyloxazol-2-yl)cyclohexane (isomer B) (128 mg) as an oil.

IR (Film) : 1755, 1600 cm$^{-1}$

NMR (CDCl$_3$, δ) : 1.0–1.1 (1H, m), 1.2–1.4 (3H, broad), 1.26 (3H, t, J=7.1Hz), 1.77 (4H, m), 2.10 (1H, m), 2.3–2.4 (1H, m), 2.6–2.7 (2H, m), 4.23 (2H, q, J=7.1Hz), 4.48 (2H, s), 6.6–6.8 (3H, m), 7.12 (1H, t, J=7.8Hz), 7.2–7.4 (6H, m), 7.5–7.7 (4H, m)

(+) APCI Mass (m$^+$/z) : 496 (M$^+$+1)

Isomer A is different from isomer B in configuration.

EXAMPLE 2

A mixture of isomer A (65 mg) obtained in Example 1 and 1N sodium hydroxide aqueous solution (0.2 ml) in 1,2-dimethoxyethane (1 ml) was stirred at room temperature for 2 hours, neutralized with 1N hydrochloric acid, diluted with water, and extracted with ethyl acetate. The extract was washed with brine, dried over magnesium sulfate, and evaporated in vacuo. The residue was triturated in n-hexane to give cis- or trans-1-[(3-carboxymethoxyphenyl)methyl]-2-(4,5-diphenyloxazol-2-yl)cyclohexane (isomer C) (60 mg) as a colorless amorphous powder.

mp : 59.2–65.9° C.

IR (Nujol +CHCl$_3$) : 1740, 1600 cm$^{-1}$

NMR (DMSO-d$_6$, δ) : 1.49 (4H, m), 1.79 (4H, m), 2.60 (1H, m), 2.5–2.6 (2H, m), 3.20 (1H, m), 4.57 (2H, s), 6.6–6.7 (3H, m), 7.1–7.2 (1H, m), 7.3–7.6 (10H, m)

Mass (m$^+$/z) : 468 (M$^+$+1)

Analysis Calcd. for C$_{30}$H$_{29}$NO$_4$.0.5H$_2$O C 75.61, H 6.35, N 2.94 Found C 75.54, H 6.45, N 2.82

EXAMPLE 3

The following compound was obtained by treating isomer B obtained in Example 1 according to a similar manner to that of Example 2.

trans- or cis-1-[(3-Carboxymethoxyphenyl)methyl]-2-(4,5-diphenyloxazol-2-yl)cyclohexane (isomer D)

mp : 54.7–61.7° C.

IR (Nujol +CHCl$_3$) : 1730, 1600 cm$^{-1}$

NMR (DMSO-d$_6$, δ) : 1.1–1.3 (4H, broad), 1.73 (4H, broad), 2.04 (1H, broad), 2.3–2.4 (1H, m), 2.6–2.7 (2H, m), 4.54 (2H, s), 6.6–6.7 (3H, broad), 7.1–7.2 (1H, broad), 7.4–7.6 (10H, m)

Analysis Calcd. for C$_{30}$H$_{29}$N$_4$.0.4H$_2$O: C 75.90, H 6.33, N 2.95 Found : C 75.86, H 6.37, N 2.81

Isomer D is different from isomer C obtained in Example 2 in configuration.

EXAMPLE 4

To a solution of a mixture of 1-(4,5-diphenyloxazol-2-yl)-2-(3-methoxybenzyl)cyclopentene and 1-(4,5-diphenyloxazol-2-yl)-5-(3-methoxybenzyl)cyclopentene (2 g) in methylene chloride (30 ml) was added boron tribromide in methylene chloride (1M, 9.8 ml) at 0C. After being stirred for 2 hours at 0° C., the solvent was evaporated in vacuo to give a residue containing a mixture of 1-(4,5-diphenyloxazol-2-yl)-2-(3-hydroxybenzyl)cyclopentene and 1-(4,5-diphenyloxazol-2-yl)-5-(3-hydroxybenzyl)-cyclopentene. The residue was diluted with ethyl acetate and the solution was washed with water and brine. The dried solvent was evaporated in vacuo. The oily residue was dissolved in N,N-dimethylformamide (20 ml). To the solution were added potassium carbonate (2.0 g) and ethyl bromoacetate (2.2 ml), and the resulting mixture was stirred for 3 hours at room temperature. The reaction solution was partitioned between ethyl acetate and water and the organic layer was washed with water and brine, dried over magnesium sulfate, and evaporated in vacuo. The oily residue was chromatographed on silica gel using n-hexane—ethyl acetate as an eluent. The first fraction gave ethyl [3-[[2-(4, 5-diphenyloxazol-2-yl)-1-cyclopenten-1-yl]methyl] phenoxy]acetate (0.38 g).

IR (Neat) : 1750 cm$^{-1}$

NMR (CDCl$_3$, δ) : 1.29 (3H, t, J=7.0Hz), 1.8–2.0 (2H, m), 2.4–2.6 (2H, m), 2.9–3.1 (2H, m), 4.10 (2H, br s), 4.21 (2H, q, J=7.0Hz), 4.50 (2H, s), 6.6–7.0 (3H, m), 7.1–7.5 (7H, m), 7.5–7.8 (4H, m)

Mass : 480 (M$^+$+1)

The second fraction gave ethyl [3-[[2-(4,5-diphenyloxazol-2-yl)-2-cyclopenten-1-yl]methyl]-phenoxylacetate (0.55 g).

IR (Neat) : 1750 cm$^{-1}$

NMR (CDCl$_3$, δ) : 1.31 (3H, t, J=7.0Hz), 1.8–2.2 (2H, m), 2.3–2.7 (3H, m), 3.3–3.6 (2H, m), 4.23 (2H, q, J=7.0Hz), 4.57 (2H, s), 6.6–7.0 (4H, m), 7.1–7.5 (7H, m), 7.5–7.8 (4H, m)

Mass : 480 (M$^+$+1)

EXAMPLE 5

A suspension of 2-[6-[(3-hydroxyphenyl)methyl]-1-cyclohexen-1-yl]-4,5-diphenyloxazole (885 mg), ethyl bromoacetate (399 mg), and potassium carbonate (360 mg) in N,N-dimethylformamide was stirred at room temperature for 3 days and partitioned between ethyl acetate and water. The organic layer was separated, washed with water (twice) and brine, dried over magnesium sulfate, and evaporated in vacuo. The oily residue was purified by column chromatography on silica gel (n-hexane—ethyl acetate (20:1)) to afford ethyl [3-[[2-(4,5-diphenyl-2-oxazolyl)-2-cyclohexen-1-yl] methyl]phenoxy]acetate (847 mg) as a solid.

IR (Neat) : 1710, 1590 cm$^{-1}$

NMR (CDCl$_3$, δ) : 1.29 (3H, t, J=7.1Hz), 1.4–1.75 (4H, br m), 2.30 (2H, br m), 2.52 (1H, dd, J=13.0, 10.4Hz), 3.13 (1H, br m), 3.29 (1H, dd, J=13.1Hz, 3.2Hz), 4.26 (2H, q, J=7.1Hz), 4.59 (2H, s), 6.71–6.76 (1H, m), 6.90–7.17 (3H, br), 7.21–7.44 (6H, m), 7.60–7.74 (4H, m)

Mass ((+) APCI) : 494 (M$^+$+1)

EXAMPLE 6

To a solution of a mixture (300 mg) of ethyl [3-[{2-(4, 5-diphenyloxazol-2-yl)-1-cyclopenten-1-yl}methyl]

phenoxy]acetate and ethyl [3-[{2-(4,5-diphenyloxazol-2-yl)-2-cyclopenten-1-yl}methyl]phenoxy]acetate in methylene chloride (10 ml) were added sodium carbonate (100 mg) and m-chloroperbenzoic acid (200 mg) at 0° C. After being stirred for 2 hours, the reaction mixture was washed with water and brine and dried over magnesium sulfate. After the solvent was evaporated, the residue containing a mixture of ethyl [3-[{2-(4,5-diphenyloxazol-2-yl)-1,2-epoxycyclopentan-1-yl}methyl]phenoxy]acetate and ethyl [3-[(2-(4,5-diphenyloxazol-2-yl)-2,3-epoxycyclopentan-1-yl]methyl]phenoxy]acetate was dissolved in a mixture of ethyl acetate-ethanol (20 ml–10 ml), and thereto was added 10% palladium on carbon (50 mg). After being stirred for 6 hours under hydrogen atmosphere, the reaction mixture was filtered. The solvent was evaporated in vacuo, the residue was chromatographed on silica gel. The first fraction gave ethyl [3-[{2-(4,5-diphenyloxazol-2-yl)-1-hydroxycyclopentan-1-yl}methyl]phenoxy]acetate (70 mg).

IR (Neat) : 3200–3300, 1750 cm$^{-1}$

NMR (CDCl$_3$, δ) : 1.26 (3H, t, J=7.6Hz), 1.5–2.3 (6H, m), 2.9–3.3 (3H, m), 4.22 (2H, q, J=7.6Hz), 4.39 (2H, s), 6.5–7.0 (4H, m), 7.0–7.8 (10H, m)

Mass : 498 (M$^+$+1)

The second fraction gave ethyl [3-[{2-(4,5-diphenyloxazol-2-yl)-3-hydroxycyclopentan-1-yl}methyl]phenoxy]acetate (110 mg).

NMR (CDCl$_3$, δ) : 1.26 (3H, t, J=7.6Hz), 1.5–2.4 (5H, m), 2.60 (1H, d, J=12Hz), 2.87 (1H, d, J=12Hz), 4.22 (2H, q, J=7.6Hz), 4.50 (2H, s), 6.5–7.0 (4H, m), 7.0–7.8 (10H, m)

Mass : 498 (M$^+$+1)

EXAMPLE 7

To a solution of ethyl [3-[[2-(4,5-diphenyloxazol-2-yl)-2-cyclopenten-1-yl]methyl]phenoxy]acetate (400 mg) in ethanol (20 ml) was added 1N-sodium hydroxide solution (0.83 ml). After being stirred for 8 hours, the solvent was evaporated in vacuo. The residue was triturated in ether to give sodium [3-[[2-(4,5-diphenyloxazol-2-yl)-2-cyclopenten-1-yl]methyl]phenoxy]acetate (350 mg).

IR (Nujol) : 3400, 1600 cm$^{-1}$

NMR (DMSO-d$_6$, δ) : 1.6–2.1 (2H, m), 2.4–2.6 (3H, m), 3.38 (2H, s), 4.08 (2H, br s), 6.6–6.8 (4H, m), 7.0–7.2 (1H, m), 7.3–7.8 (10H, m)

FAB Mass : 474 (M$^+$+1)

EXAMPLE 8

The following compounds were obtained according to a similar manner to that of Example 7.

(1) Sodium [3-[{2-(4,5-diphenyloxazol-2-yl)-1-cyclopenten-1-yl}methyl]phenoxy]acetate NMR (DMSO-d$_6$, δ) : 1.8–2.0 (2H, m), 2.8–3.0 (2H, m), 4.03 (4H, m), 6.5–6.8 (3H, m), 7.12 (1H, t, J=8Hz), 7.3–7.8 (10H, m)

FAB Mass : 474 (M$^+$+1)

(2) Sodium [3-[{2-(4,5-diphenyloxazol-2-yl)-1-hydroxycyclopentan-1-yl}methyl]phenoxy]acetate IR (Nujol) : 1600 cm$^{-1}$ NMR (DMSO-d$_6$, δ) : 1.4–2.2 (4H, m), 2.8–3.2 (2H, m), 4.04 (2H, s), 6.6 (2H, m), 6.9 (1H, m), 7.1 (1H, m), 7.2–8.0 (10H, m)

FAB Mass : 492 (M$^+$+1)

(3) Sodium [3-[{2-(4,5-diphenyloxazol-2-yl)-3-hydroxycyclopentan-1-yl}methyl]phenoxy]acetate IR (Nujol) : 1600 cm$^{-1}$ NMR (DMSO-d$_6$, δ) : 1.4–2.0 (4H, m), 2.0–2.3 (2H, m), 4.01 (2H, s), 6.4–6.8 (3H, m), 7.02 (1H, t, J=8.0Hz), 7.2–7.9 (10H, m)

FAB Mass : 492 (M$^+$+1)

EXAMPLE 9

A solution of ethyl [3-[[2-(4,5-diphenyl-2-oxazolyl)-2-cyclohexen-1-yl]methyl]phenoxy]acetate (355 mg) and 1N sodium hydroxide aqueous solution (0.71 ml) in 1,2-dimethoxyethane (6 ml) and ethanol (6 ml) was stirred at room temperature for 2 hours and evaporated in vacuo. The solid residue was washed with diethyl ether to afford sodium [3-[[2-(4,5-diphenyl-2-oxazolyl)-2-cyclohexen-1-yl] methyl]phenoxy]acetate (308 mg) as a pale yellow powder.

mp : 244–249° C. (dec.)

IR (Nujol) : 1625, 1590, 1250 cm$^{-1}$

NMR (DMSO-d$_6$, δ) : 1.35–1.85 (4H, m), 2.1S–2.6S (3H, m), 2.95–3.2 (2H, m), 4.08 (2H, s), 6.65 (1H, br d, J=8.0Hz), 6.77–6.81 (2H, m), 7.10 (1H, m), 7.14 (1H, t, J=8.0Hz), 7.37–7.52 (6H, m), 7.59–7.70 (4H, m)

FAB Mass (m/z) : 488 (M$^+$+1), 510 (M$^+$+Na)

Analysis Calcd. for C$_{30}$H$_{26}$NNaO$_4$.0.9H$_2$O C 71.53; H 5.56; N 2.78 Found : C 71.43, H 5.52, N 2.74

EXAMPLE 10

To a solution of a mixture (400 mg) of ethyl [3-[{2-(4,5-diphenyloxazol-2-yl)-1-cyclopenten-1-yl}methyl]phenoxy]acetate and ethyl [3-[{2-(4,5-diphenyloxazol-2-yl)-2-cyclopenten-1-yl}methyl]phenoxy]acetate in a mixture of ethanol (10 ml) and ethyl acetate (10 ml) was added 10% palladium on carbon (50 mg). After being stirred for 6 hours under hydrogen atmosphere, the reaction mixture was filtered. The solvent was evaporated in vacuo to give a residue containing a mixture of ethyl [3-[{(1RS,2RS)-2-(4,5-diphenyloxazol-2-yl)cyclopentan-1-yl}methyl]phenoxy] acetate and ethyl [3-[{(1RS,2SR)-2-(4,5-diphenyloxazol-2-yl)cyclopentan-1-yl}methyl]phenoxy]acetate. The residue was dissolved in ethanol (20 ml), and 1N-sodium hydroxide solution (0.80 ml) was added. After being stirred for 8 hours, the solvent was evaporated in vacuo. The residue was triturated in ether to give a mixture (350 mg) of sodium [3-[{(1RS,2RS)-2-(4,5-diphenyloxazol-2-yl)cyclopentan-1-yl}methyl]phenoxy]acetate and sodium [3-[{(1RS,2SR)-2-(4,5-diphenyloxazol-2-yl)cyclopentan-1-yl}methyl] phenoxy]acetate.

NMR (DMSO-d$_6$, δ) : 1.2–2.4 (6H, m), 2.4–2.7 (2H, m), 2.7–2.9 (1H, m), 4.05 (2H, s), 6.5–6.9 (3H, m), 7.05 (1H, t, J=8.0Hz), 7.3–7.9 (10H, m)

FAB Mass : 476 (M$^+$+1)

EXAMPLE 11

A mixture (200 mg) of sodium [3-[{(1RS,2SR)-2-(4,5-diphenyloxazol-2-yl)cyclopentan-1-yl}methyl]phenoxy] acetate (trans compound) and sodium [3-[{(1RS,2RS)-2-(4,5-diphenyloxazol-2-yl)cyclopentan-1-yl}methyl]phenoxy]-acetate (cis compound) was separated by HPLC to give trans compound (20 mg) and cis compound (110 mg).

trans compound

NMR (DMSO-d$_6$, δ) : 1.2–2.4 (6H, m), 2.4–3.0 (3H, m), 4.00 (2H, s), 6.5–6.8 (3H, m), 7.04 (1H, t, J=8.0Hz), 7.3–7.9 (10H, m)

cis compound

NMR (DMSO-d$_6$, δ) : 1.4–2.4 (6H, m), 4.00 (2H, s), 6.5–6.8 (3H, m), 7.04 (1H, t, j=8.0Hz), 7.3–7.9 (10H, m)

EXAMPLE 12

The following compounds were obtained according to a similar manner to that of Example 4.

(1) Ethyl [3-2-(4,5-diphenyloxazol-2-yl)cyclopropan-1-yl]phenoxy]acetate

IR (Neat) : 1720 cm$^{-1}$

NMR (CDCl$_3$, δ) : 1.26 (3H, t, j=7.0Hz), 1.4–1.6 (1H, m), 1.7–1.9 (1H, m), 2.3–2.5 (1H, m), 2.6–2.8 (1H, m), 4.25 (2H, q, J=7.0Hz), 4.61 (2H, s), 6.7–6.9 (3H, m), 7.1–7.8 (11H, m)

Mass : 440 (M$^+$+1)

(2) Ethyl [3-[2-[(4,5-diphenyloxazol-2-yl)methyl]-1-cyclopenten-1-yl]phenoxy]acetate IR (Neat) : 1740, 1600 cm$^{-1}$ NMR (CDCl$_3$, δ) : 1.27 (3H, t, J=7Hz), 1.8–2-.0 (2H, m), 2.4–2.8 (4H, m), 3.76 (2H, s), 4.20 (2H, q, J=7Hz), 4.68 (2H, s), 6.6–6.9 (1H, m), 7.0–7.2 (2H, m), 7.2–7.8 (11H, m)

Mass : 480 (M$^+$+1)

(3) Ethyl [3-[2-[(4,5-diphenyloxazol-2-yl)methylene]cyclohexan-1-yl]phenoxy]acetate IR (Neat) : 1750, 1640 cm$^{-1}$ NMR (CDCl$_3$, δ) : 1.22 (3H, t, J=7Hz), 1.5–2.5 (7H, m), 3.3–3.6 (1H, m), 3.7–4.0 (1H, m), 4.17 (2H, q, J=7Hz), 4.62 (2H, s), 6.7–7.0 (3H, m), 7.2–7.8 (11H, m)

Mass : 494 (M$^+$+1)

(4) Ethyl [3-[2-[(4,5-diphenyloxazol-2-yl)methyl]-1-cyclohexen-1-yl]phenoxy]acetate IR (Neat) : 1750 cm$^{-1}$ NMR (CDCl$_3$, δ) : 1.22 (3H, t, J=7Hz), 1.6–1.8 (4H, m), 2.0–2.4 (4H, m), 3.46 (2H, s), 4.20 (2H, q, J=7Hz), 4.59 (2H, s), 6.7–7.0 (3H, m), 7.2–7.8 (11H, m)

Mass : 494 (M$^+$+1)

(5) 2-[2-[3-Ethoxycarbonylmethoxybenzyl]cyclohexylidene]-methyl]-4,5-diphenyloxazole IR (Neat) : 1750, 1650, 1610 cm$^{-1}$ NMR (CDCl$_3$, δ) : 1.24 (3H, t, J=7.0Hz), 1.3–1.9 (6H, m), 2.2–3.0 (5H, m), 4.25 (2H, a, J=7.0Hz), 4.68 (2H, s), 6.11 (1H, s), 6.6–6.9 (3H, m), 7.0–7.8 (11H, m)

Mass : 508 (M$^+$+1)

(6) Ethyl [3-[[3-(4,5-diphenyloxazol-2-yl)cyclohexan-1-yl]methyl]phenoxy]acetate IR (Neat) : 1750, 1605 cm$^{-1}$ NMR (CDCl$_3$, δ) : 1.29 (3H, t, J=7Hz), 0.9–2.4 (9H, m), 2.5–2.7 (2H, m), 2.8–3.3 (1H, m), 4.25 (2H, q, J=7Hz), 4.57, 4.60 (2H, each s), 6.6–6.9 (3H, m), 7.0–7.8 (11H, m)

Mass : 496 (M$^+$+1)

(7) Ethyl [3-[3-(4,5-diphenyloxazol-2-yl)cyclopentan-1-yl]phenoxy]acetate

IR (Neat) : 1750, 1600 cm$^{-1}$

NMR (CDCl$_3$, δ) : 1.28 (3H, t, J=7Hz), 1.8–2.6 (6H, m), 3.1–3.8 (2H, m), 4.28 (2H, q, J=7Hz), 4.61, 4.62 (2H, each s), 6.6–7.0 (3H, m), 7.2–7.8 (11H, m)

Mass : 468 (M$^+$+1)

(8) Ethyl [3-[3-(4,5-diphenyloxazol-2-yl)cyclohexan-1-yl]phenoxy]acetate

IR (Neat) : 1750, 1605 cm$^{-1}$

NMR (CDCl$_3$, δ) : 1.29 (3H, t, J=7Hz), 1.4–2.9 (9H, m), 2.9–3.1 (1H, m), 4.28 (2H, q, J=7Hz), 4.61 (2H, s), 6.6–7.0 (3H, m), 7.2–7.8 (11H, m)

Mass : 482 (M$^+$+1)

(9) Ethyl [3-[[(1R)-2-(4,5-diphenyloxazol-2-yl)-2-cyclohexen-1-yl]methyl]phenoxy]acetate HPLC (chiralcel AD, 5% isopropanol/hexane, 1 ml/min); rt=11.9 min

(10) Ethyl [3-[[(1S)-2-(4,5-diphenyloxazol-2-yl)-2-cyclohexen-1-yl]methyl]phenoxy]acetate HPLC (chiralcel AD, 5% isopropanol/hexane, 1 ml/min); rt=6.9 min

EXAMPLE 13

To a solution of (+)-(5S)-1-(4,5-diphenyloxazol-2-yl)-5-(3-methoxybenzyl)cyclopentene (2.33 g) in methylene chloride (10 ml), was added boron tribromide in methylene chloride (1M, 9 ml) at 0C. After 3.5 hours stirring at the same temperature, the reaction mixture was washed with water and saturated aqueous sodium hydrogencarbonate. Drying (sodium sulfate) and removal of solvent afforded a yellow syrup containing (+)-(5S)-1-(4,5-diphenyloxazol-2-yl)-5-(3-hydroxybenzyl)cyclopentene. An acetonitrile solution (20 ml) of the yellow syrup, potassium carbonate (1.30 g), methyl bromoacetate (0.98 g) and potassium iodide (a catalytic amount) was stirred under reflux for 3.5 hours. The solvent was evaporated in vacuo and the residue was partitioned between ethyl acetate and 1N hydrochloric acid. The organic layer was washed with 1N hydrochloric acid, water and brine. Drying (sodium sulfate) and removal of solvent at reduced pressure followed by flash chromatography over 50 g of silica afforded (+)-methyl [3-[[(1S)-2-(4,5-diphenyloxazol-2-yl)-2-cyclopenten-1-yl]methyl]phenoxy]acetate (2.10 g, 98.2% ee) as a yellow oil.

[α]$_D$:+51.68° (C=1.085, CH$_2$Cl$_2$)

IR (Film) : 1735, 1700, 1650, 1600 cm$^{-1}$

NMR (CDCl$_3$, δ) : 1.79–1.90 (1H, m), 1.95–2.15 (1H, m), 2.41–2.44 (2H, m), 2.61 (1H, dd, J=13.3Hz, 9.5Hz), 3.39 (1H, dd, J=13.3Hz, 4.1Hz), 3.55 (1H, m), 3.78 (3H, s), 4.59 (2H, s), 6.69–6.92 (4H, m), 7.15–7.42 (7H,m), 7.59–7.72 (4H, m)

Mass (APCI) m/e : 466 (M$^+$+1)

EXAMPLE 14

The following compound was obtained according to a similar manner to that of Example 13.

(−)-Methyl [3-[[(1R)-2-(4,5-diphenyloxazol-2-yl)-1-cyclopenten-1-yl]methyl]phenoxy]acetate

[α]$_D$: −48.22° (C=1.065, CH$_2$Cl$_2$)

IR (Film) 1735, 1700, 1650, 1600 cm$^{-1}$

NMR (CDCl$_3$, δ) : 1.79–1.90 (1H, m), 1.95–2.15 (1H, m), 2.41–2.44 (2H, m), 2.61 (1H, dd, J=13.3Hz, 9.5Hz), 3.39 (1H, dd, J=13.3Hz, 4.1Hz), 3.55 (1H, m), 3.78 (3H, s), 4.59 (2H, s), 6.69–6.92 (4H, m), 7.15–7.42 (7H, m), 7.59–7.72 (4H, m)

Mass (APCI) m/e : 466 (M$^+$+1)

EXAMPLE 15

The following compounds were obtained according to a similar manner to that of Example 5.

(1) Ethyl 3'-(4,5-diphenyl-2-oxazolyl)-3-biphenylyloxyacetate

IR (Nujol) : 1745, 1605 cm$^{-1}$

NMR (CDCl$_3$, δ) : 1.30 (3H, t, J=7.1Hz), 4.30 (2H, q, J=7.1Hz), 4.71 (2H, s), 6.94–6.95 (1H, m), 7.25–7.45 (9H, m), 7.55–7.77 (6H, m), 8.13–8.17 (1H, m), 8.35–8.37 (1H, m)

(+) APCI Mass : 476(M$^+$+1)

(2) Ethyl [3-[trans-2-hydroxy-2-(4,5-diphenyl-2-oxazolyl)cyclohexyl]phenoxy]acetate IR (Neat) : 3450, 1755, 1600 cm$^{-1}$ NMR (CDCl$_3$, δ) : 1.29 (3H, t, J=7.1Hz), 1.58 (1H, br m), 1.86–2.04 (4H, br m), 2.23–2.37 (3H, br m), 2.91–2.99 (1H, dd, J=13.1Hz, 3.5Hz), 3.35 (1H, s), 4.26 (2H, q, J=7.1Hz), 4.41 (2H, s), 6.5–6.7 (3H, m), 7.07–7.25 (1H, m), 7.31–7.39 (6H, m), 7.50–7.58 (4H, m)

(+) APCI Mass : 498 (M$^+$+1)

(3) Methyl [3-[[trans-2-hydroxy-2-(4,5-diphenyl-2-oxazolyl)cyclohexyl]methyl]phenoxy]acetate IR (Neat) : 3430, 1760, 1600 cm$^{-1}$ NMR (CDCl$_3$, δ) : 1.3–2.0 (7H, br m), 2.04–2.20 (3H, m), 3.06–3.11 (1H, br m), 3.47 (1H, s), 3.79 (3H, s), 4.58 (2H, s), 6.68–6.82 (3H, m), 7.13–7.18 (1H, m), 7.3–7.4 (6H, m), 7.6–7.7 (4H, m)

(+) APCI Mass : 498 (M$^+$+1)

(4) Ethyl [3-[[2-[4,5-bis(4-methylphenyl)-2-oxazolyl]-2-cyclohexen-1-yl]methyl]phenoxy]acetate IR (Neat) : 1735, 1590 cm$^{-1}$ NMR (CDCl$_3$, δ) : 1.29 (3H, t, J=7.1Hz), 1.39–1.74 (4H, br m), 2.29–2.37 (2H, br m), 2.45–2.69 (1H, br m), 3.11–3.32 (2H, br m) , 4.26 (2H, q, J=7.1Hz), 4.59 (2H, s), 6.71–6.76 (1H, m), 6.86–6.99 (3H, m), 7.15–7.20 (5H, m), 7.37–7.62 (4H, m)

(+) APCI Mass : 522 (M$^+$+1)

(5) Ethyl [3-[[2-[4,5-bis(4-methylphenyl)-2-oxazolyl]-2-cyclopenten-1-yl]methyl]phenoxy]acetate IR (Neat) : 1750, 1590 cm$^{-1}$ NMR (CDCl$_3$, δ) : 1.28 (3H, t, J=7.1Hz), 1.78–1.87 (1H, m), 1.89–2.13 (1H, m), 2.38 (6H, s), 2.43–2.64 (3H, br m), 3.35–3.53 (2H, br m), 4.25 (2H, q, J=7.1Hz), 4.58 (2H, s), 6.67–6.75 (2H, m), 6.83–6.91 (2H, m), 7.15–7.25 (5H, m), 7.48–7.60 (4H, m)

(+) APCI Mass : 508 (M$^+$+1)

(6) Ethyl [3-[[cis-2-hydroxy-2-(4,5-diphenyl-2-oxazolyl)cyclohexyl]methyl]phenoxy]acetate IR (Nujol) : 3465, 1740, 1600 cm$^{-1}$ NMR (CDCl$_3$, δ) : 1.28 (3H, t, J=7.1Hz), 1.4–1.9 (8H, br), 2.28–2.66 (3H, m), 3.23 (1H, s), 4.23 (2H, q, J=7.1Hz), 4.41 (2H, s), 6.56–6.72 (3H, m), 7.07–7.11 (1H, m), 7.19–7.43 (6H, m), 7.50–7.55 (2H, m), 7.61–7.66 (2H, m)

(+) APCI Mass : 512 (M$^+$+1)

(7) Methyl [3-[[2-(4,5-diphenyl-2-oxazolyl)phenyl]-methyl]phenoxy]acetate

IR (Neat) : 1760, 1600 cm$^{-1}$

NMR (CDCl$_3$, δ) : 3.74 (3H, s), 4.50 (2H, s), 4.61 (2H, s), 6.71–6.87 (3H, m), 7.14–7.42 (10H, m), 7.55–7.66 (2H, m), 7.69–7.74 (2H, m), 8.10–8.15 (1H, m)

(+) APCI Mass : 476 (M$^+$+1)

EXAMPLE 16

A mixture of 2-[2-(3-hydroxyphenylmethyl)cyclohexyl]-4,5-bis(4-methylphenyl)oxazole, ethyl bromoacetate and potassium carbonate was stirred in acetonitrile at room temperature overnight. Ethyl acetate and water were added to the reaction mixture. The organic layer was separated and washed with water, and next brine. The organic layer was dried on magnesium sulfate and evaporated to the crude oil. The crude oil was purified with SiO$_2$. To afford a mixture of ethyl [3-[[cis- or trans-2-[4,5-bis(4-methylphenyl)-2-oxazolyl]cyclohexyl]methyl]phenoxy]acetate (isomer G) and ethyl [3-[[trans- or cis-2-[4,5-bis(4-methylphenyl)-2-oxazolyl]cyclohexyl]methyl]phenoxy]acetate (isomer H).

Isomer G is different from isomer H in configuration.

Isomer G

IR (Neat) : 1760, 1600 cm$^{-1}$

NMR (CDCl$_3$, δ) : 1.27 (3H, t, J=7.1 Hz), 1.3–2.05 (8H, br m), 2.30 (1H, br m), 2.37 (6H, s), 2.50–2.72 (2H, m), 3.20–3.23 (1H, m), 4.24 (2H, q, J=7.1Hz), 4.53 (2H, s), 6.66–6.78 (3H, m), 7.10– 7.20 (5H, m), 7.45–7.59 (4H, m)

(+) APCI Mass : 524 (M$^+$+1)

Isomer H

IR (Neat) : 1750, 1600 cm$^{-1}$

NMR (CDCl$_3$, δ) : 1.28 (3H, t, J=7.1Hz), 1.76 (6H, br m), 2.1 (2H, br m), 2.29 (1H, br m), 2.37 (6H, s), 2.65–2.72 (3H, br m), 4.24 (2H, q, J=7.1Hz), 4.49 (2H, s), 6.63–6.76 (3H, m), 7.07–7.18 (5H, m), 7.42–7.55 (4H, m)

(+) APCI Mass :524 (M$^+$+1)

EXAMPLE 17

To a solution of ethyl [3-[2-[(4,5-diphenyloxazol-2-yl)methyl]-1-cyclopenten-1-yl]phenoxy]acetate (600 mg) in a mixture of acetonitrile (10 ml) and water (5 ml) were added N-methylmorpholine N-oxide (0.5 ml, 60% solution in water) and osmium(VIII) oxide (2 ml, 2.5% solution in t-butyl alcohol) at room temperature. After being stirred for 20 hours, the mixture was poured into a mixture of ethyl acetate and water. The organic layer was washed with saturated sodium bicarbonate aqueous solution and brine and concentrated, and the residue was purified by column chromatography on silica gel to give ethyl [3-[2-[(4,5-diphenyloxazol-2-yl)methyl]-1,2-dihydroxycyclopentyl]phenoxy]acetate (210 mg).

NMR (CDCl$_3$, δ) : 1.27 (3H, t, J=7Hz), 1.8–2.4 (6H, m), 2.68 (1H, d, J=17Hz), 2.78 (1H, d, J=17Hz), 4.24 (2H, q, J=7Hz), 4.50 (2H, s), 6.7–7.0 (3H, m), 7.0–7.8 (11H, m)

Mass : 514 (M$^+$+1)

EXAMPLE 18

The following compound was obtained according to a similar manner to that of Example 17.

Ethyl [3-[2-[(4,5-diphenyloxazol-2-yl)methyl]-1,2-dihydroxycyclohexyl]phenoxy]acetate IR (Neat) : 3400, 1750 cm$^{-1}$ NMR (CDCl$_3$, δ) : 1.22 (3H, ,t, J=7Hz), 1.4–2.4 (8H, m), 3.00 (1H, d, J=16Hz), 3.03 (1H, d, J=16Hz), 4.12 (2H, t, J=7Hz), 4.95 (2H, s), 6.6–6.8 (1H, m), 7.0–7.6 (10H, m)

Mass : 528 (M$^+$+1)

EXAMPLE 19

To a solution of ethyl [3-[2-[(4,5-diphenyloxazol-2-yl)methyl]-1-cyclopenten-1-yl]phenoxy]acetate (1.0 g) in methylene chloride (20 ml) were added m-chloroperbenzoic acid (540 mg) and sodium carbonate (330 mg) at room temperature. After being stirred for 4 hours, the mixture was washed with saturated sodium bicarbonate aqueous solution and brine. The dried solvent was evaporated and the residue was purified by column chromatography on silica gel to give ethyl [3-[2-[(4,5-diphenyloxazol-2-yl)methyl]-1,2-epoxycyclopentyl]phenoxy]acetate (700 mg).

IR (Neat) : 1750 cm$^{-1}$

NMR (CDCl$_3$, δ) : 1.25 (3H, t, J=7Hz), 1.4–2.4 (6H, m), 2.90 (1H, d, J=14Hz), 3.10 (1H, d, J=14Hz), 4.24 (2H, q, J=7Hz), 4.58 (2H, s), 6.7–7.0 (3H, m), 7.0–7.9 (11H, m)

Mass : 496 (M$^+$+1)

EXAMPLE 20

60% Sodium hydride (18 mg) was added to a stirred solution of ethyl [3-[[cis-2-(4,5-diphenyl-2-oxazolyl)-2-hydroxycyclohexyl]methyl]phenoxy]acetate (210 mg) and methyl iodide (58 mg) in N,N-dimethylformamide (2.5 ml) at room temperature and the resulting mixture was stirred at the same temperature for 40 minutes. The reaction mixture was partitioned between ethyl acetate and 0.1N hydrochloric acid. The organic layer was washed successively with water (three times), sodium bicarbonate aqueous solution, and brine, dried over magnesium sulfate, and evaporated in vacuo. The residue was chromatographed (n-hexane - ethyl acetate) over silica gel to afford ethyl [3-[[cis-2-(4,5-diphenyl-2-oxazolyl)-2-methoxycyclohexyl]-methyl] phenoxy]acetate (110 mg) as a colorless oil.

IR (Neat) : 1750, 1600 cm$^{-1}$

NMR (CDCl$_3$, δ) : 1.27 (3H, t, J=7.1Hz), 1.40–2.00 (6H, br m), 2.14–2.27 (3H, m), 2.55 (1H, dd, J=13.7Hz, 10.3Hz), 2.84 (1H, dd, J=13.7Hz, 3.6Hz), 3.45 (3H, s), 4.24 (2H, q, J=7.1Hz), 4.50 (2H, s), 6.62 (3H, m), 7.07–7.16 (1H, m), 7.31–7.41 (6H, m), 7.57–7.69 (4H, m)

(+) APCI Mass : 526 (M$^+$+1)

EXAMPLE 21

To a solution of ethyl [3-2-[(4,5-diphenyloxazol-2-yl) methyl]-1-cyclopenten-1-yl]phenoxy]acetate (0.5 g) in ethanol (20 ml) was added 10% palladium on carbon (100 mg). After being stirred for 6 hours under hydrogen atmosphere, the reaction mixture was filtered. The solvent was evaporated in vacuo to give ethyl [3-2-[(4,5-diphenyloxazol-2-yl)methyl]cyclopentyl]phenoxy]acetate (400 mg).

IR (Neat) : 1750, 1600 cm$^{-1}$

NMR (CDCl$_3$, δ) : 1.25 (3H, t, J=7Hz), 1.6–2.3 (6H, m), 2.3–2.7 (2H, m), 2.8–3.0 (1H, m), 3.2–3.4 (1H, m), 4.20 (2H, q, J=7Hz), 4.54 (2H, s), 6.6–6.9 (3H, m), 7.2–7.7 (11H, m)

Mass : 482 (M$^+$+1)

EXAMPLE 22

To a solution of ethyl [3-2-[(4,5-diphenyloxazol-2-yl) methyl]- 1,2-epoxycyclopentyl]phenoxy]acetate (500 mg) in ethanol (20 ml) was added palladium on carbon (0.5 g). After being stirred for 24 hours under hydrogen atmosphere, the reaction mixture was filtered. The solvent was evaporated in vacuo to give ethyl [3-2-[(4,5-diphenyloxazol-2-yl)methyl]-2-hydroxycyclopentyl]phenoxy]-acetate (260 mg).

IR (Neat) : 3400, 1750 cm$^{-1}$

NMR (CDCl$_3$, δ) : 1.22 (3H, t, J=7Hz), 1.6–2.5 (6H, m), 2.5–3.0 (2H, m), 4.10 (2H, q, J=7Hz), 4.42, 4.47 (2H, each s), 6.6–7.0 (3H, m), 7.0–7.8 (11H, m)

Mass : 498 (M$^+$+1)

EXAMPLE 23

To a solution of ethyl [3-2-[(4,5-diphenyloxazol-2-yl) methylene]cyclohexan-1-yl]phenoxy]acetate (300 mg) in a mixture of ethanol (10 ml) and tetrahydrofuran (10 ml) was added 10% palladium on carbon (50 mg). After being stirred for 4 hours under hydrogen atmosphere, the reaction mixture was filtered. The solvent was evaporated in vacuo to give ethyl [3-2-[(4,5-diphenyloxazol-2-yl)methyl]cyclohexan-1-yl]phenoxy]acetate (210 mg).

IR (Neat) : 1750 cm$^{-1}$

NMR (CDCl$_3$, δ) : 1.23 (3H, t, J=7Hz), 1.2–2.2 (9H, m), 2.3–2.9 (3H, m), 4.17 (2H, q, J=7Hz), 4.59 (2H, s), 6.6–7.0 (3H, m), 7.1–7.7 (11H, m)

Mass : 496 (M$^+$+1)

EXAMPLE 24

The following compound was obtained according to a similar manner to that of Example 23.

Ethyl [3-[[2-[(4,5-diphenyloxazol-2-yl)methyl] cyclohexyl]methyl]phenoxy]acetate IR (Neat) : 1750 cm$^{-1}$ NMR (CDCl$_2$, δ) : 1.25 (3H, t, J=7Hz), 1.1–2.2 (9H, m), 2.2–2.6 (2H, m), 2.7–3.0 (2H, m), 3.0–3.2 (1H, m), 4.26 (2H, q, J=7Hz), 7.56 (2H, s), 6.6–6.9 (3H, m), 7.0–7.4 (7H, m), 7.4–7.8 (4H, m)

Mass : 510 (M$^+$+1)

EXAMPLE 25

To a solution of (+)-methyl [3-[[(1S)-2-(4,5-diphenyloxazol-2-yl)-2-cyclopenten-1-yl]methyl]phenoxy] acetate (1.92 g) in ethanol (30 ml) was added 1N-aqueous sodium hydroxide (4.1 ml). The reaction mixture was stirred for 1 hour at room temperature. Ether (50 ml) was added to the solution. The precipitated solid was collected by filtration to afford (+)-sodium [3-[[(1S)-2-(4,5-diphenyloxazol-2-yl)-2-cyclopenten-1-yl]methyl]phenoxy]acetate (0.83 g).

[α]$_D$: +71.75° (C=0.56, MeOH)

mp : 220° C. (dec.)

IR (Nujol) : 1650, 1620, 1590 cm$^{-1}$

NMR (CD$_3$OD, δ) : 1.95–2.07 (2H, m), 2.50–2.67 (3H, m), 3.19–3.28 (1H, m), 3.55 (1H, m), 4.31 (2H, s), 6.69–6.86 (4H, m), 7.07–7.15 (1H, m), 7.35–7.58 (10H, m)

EXAMPLE 26

The following compounds were obtained according to similar manners to those of Examples 2, 7, 9 and 25.

(1) Sodium [3-2-(4,5-diphenyloxazol-2-yl)cyclopropyl] phenoxy]acetate

IR (Nujol) : 1605 cm$^{-1}$

NMR (DMSO-d$_6$, δ) : 1.5–1.9 (2H, m), 2.3–2.5 (1H, m), 2.5–2.7 (1H, m), 4.37 (2H, m), 6.7–6.9 (3H, m), 7.1–7.7 (11H, m)

FAB Mass : 434 (M$^+$+1)

(2) Sodium [3-[2-[4,5-diphenyloxazo1–2-yl)methyl]-1-cyclopenten-1-yl]phenoxy]acetate IR (Nujol) : 1610 cm$^{-1}$ NMR (DMSO-d$_6$, δ) : 1.8–2.2 (2H, m), 2.4–3.0 (2H, m), 3.70 (2H, s) 4.10 (2H, s), 6.6–7.0 (3H, m), 7.1–7.9 (11H, m)

FAB Mass : 474 (M$^+$+1)

(3) Sodium [3-2-[(4,5-diphenyloxazol-2-yl)methyl] cyclopentyl]phenoxy]acetate

IR (Nujol) : 1640 cm$^{-1}$

NMR (DMSO-d$_6$, δ) : 1.4–2.3 (6H, m), 2.4–2.7 (2H, m), 2.8–3.1 (1H, m), 3.2–3.4 (1H, m), 4.29 (2H, s), 6.6–6.9 (3H, m), 7.13 (1H, t, J=8Hz), 7.2–7.7 (10H, m)

FAB Mass : 476 (M$^+$+1)

(4) [3-2-[(4,5-Diphenyloxazol-2-yl)methyl]-1,2-dihydroxycyclopentyl]phenoxy]acetic acid IR (Neat) : 1720 cm$^{-1}$ NMR (CDCl$_3$, δ) : 1.8–3.0 (8H, m), 4.30 (2H, s), 6.7–7.0 (3H, m), 7.0–7.7 (11H, m)

FAB Mass : 486 (M$^+$+1)

(5) [3-2-[(4,5-Diphenyloxazol-2-yl)methyl]-2-hydroxypentyl]phenoxy]acetic acid

IR (Nujol) : 1720 cm$^{-1}$

NMR (CDCl$_3$, δ) : 1.4–2.2 (6H, m), 2.8–3.0 (1H, m), 3.2–3.4 (1H, m), 4.42–4.48 (2H, each s), 6.6–7.0 (3H, m), 7.0–7.6 (11H, m)

Mass : 470 (M$^+$+1)

(6) Sodium [3-[2-[(4,5-diphenyloxazol-2-yl)methylene]-cyclohexyl]phenoxy]acetate
IR (Nujol) : 1620 cm$^{-1}$
NMR (DMSO-d$_6$, δ) : 1.4–2.5 (7H, m), 3.4–3.8 (2H, m), 4.07 (2H, s), 5.52 (1H, s), 6.6–6.8 (3H, m), 7.1–7.7 (11H, m)
FAB Mass : 488 (M$^+$+1)

(7) Sodium [3-[2-[(4,5-diphenyloxazol-2-yl)methyl]cyclohexyl]phenoxy]acetate
IR (Nujol) : 1620 cm$^{-1}$
NMR (DMSO-d$_6$, δ) : 1.2–2.0 (8H, m), 2.8–3.0 (2H, m), 4.04 (2H, s), 6.5–6.8 (3H, m), 7.0–7.6 (11H, m)
FAB Mass : 490 (M$^+$+1)

(8) Sodium [3-[2-[(4,5-diphenyloxazol-2-yl)methyl]-1-cyclohexen-1-yl]phenoxy]acetate
IR (Nujol) : 1640 cm$^{-1}$
NMR (DMSO-d$_6$, δ) : 1.6–1.8 (4H, m), 2.0–2.4 (4H, m), 3.45 (2H, s), 4.07 (2H, s), 6.6–6.8 (3H, m), 7.1–7.7 (11H, m)
FAB Mass : 488 (M$^+$+1)

(9) Sodium [3-[2-[(4,5-diphenyioxazol-2-yl)methyl]-1,2-dihydroxycyclohexyl]phenoxy]acetate
IR (Nujol) : 1600 cm$^{-1}$
NMR (DMSO-d$_6$, δ) : 1.4–2.0 (8H, m), 4.07 (2H, s), 6.6–6.8 (1H, m), 7.0–7.2 (3H, m), 7.2–7.6 (10H, m)
FAB Mass : 522 (M$^+$+1)

(10) Sodium [3-[2-[(4,5-diphenyloxazol-2-yl)methylene]cyclohexylmethyl]phenoxy]acetate
IR (Nujol) : 1630, 1600 cm$^{-1}$
NMR (DMSO-d$_6$, δ) : 1.2–1.8 (6H, m), 2.2–3.2 (5H, m), 4.03 (2H, s), 6.10 (1H, s), 6.5–6.8 (3H, m), 7.0–7.7 (11H, m)
FAB Mass : 502 (M$^+$+1)

(11) Sodium [3-[2-[(4,5-diphenyloxazol-2-yl)methyl]cyclohexylmethyl]phenoxy]acetate
IR (Nujol) : 3400, 1640, 1600 cm$^{-1}$
NMR (DMSO-d$_6$, δ) : 0.8–2.0 (10H, m), 2.1–2.4 (1H, m), 2.5–3.3 (3H, m), 4.07 (2H, s), 6.5–6.8 (3H, m), 7.02 (1H, t, J=8Hz), 7.3–7.8 (10H, m)
FAB Mass : 508 (M$^+$+1)

(12) Sodium [3-[3-(4,5-diphenyloxazol-2-yl)cyclohexylmethyl]phenoxy]acetate
IR (Nujol) : 3300–3400, 1610 cm$^{-1}$
NMR (DMSO-d$_6$, δ) : 0.8–2.2 (9H, m), 4.07 (2H, s), 6.5–6.8 (3H, m), 7.10 (1H, t, J=10), 7.2–7.7 (10H, m)
FAB Mass : 490 (M$^+$+1)

(13) Sodium [3-[3-(4,5-diphenyloxazol-2-yl)cyclopentyl]phenoxy]acetate
IR (Nujol) : 1620 cm$^{-1}$
NMR (DMSO-d$_6$, δ) : 1.6–2.6 (6H, m), 3.0–3.7 (2H, m), 4.08 (2H, s), 6.6–6.8 (3H, m), 7.13 (1H, t, J=8Hz), 7.2–7.7 (10H, m).
FAB Mass : 462 (M$^+$+1)

(14) Sodium [3-[3-(4,5-diphenyloxazol-2-yl)cyclohexyl]phenoxy]acetate
IR (Nujol) : 1610 cm$^{-1}$
NMR (DMSO-d$_6$, δ) : 1.4–2.4 (8H, m), 2.5–3.2 (2H, m), 4.06 (2H, s), 6.6–6.9 (3H, m), 7.12 (1H, t, J=8Hz), 7.3–7.7 (10H, m)
FAB Mass : 476 (M$^+$+1)

(15) (−)-Sodium [3-[[(1R)-2-(4,5-diphenyloxazol-2-yl)-2-cyclohexen-1-yl]methyl]phenoxy]acetate
HPLC (chiral-AGP, 20% acetonitrile/0.02M phosphoric buffer (pH 7.0), 0.8 ml/min); rt=6.0 min
[α]$_D$: −94.5° (C=0.20, MeOH)

(16) (+)-Sodium [3-[[(1S)-2-(4,5-diphenyloxazol-2-yl)-2-cyclohexen-1-yl]methyl]phenoxy] acetate
HPLC (chiral-AGP, 20% acetonitrile/0.02M phosphoric buffer (pH 7.0), 0.8 ml/min); rt=4.0 min
[α]$_D$: +93.0° (C=0.20, MeOH)

(17) Sodium [3'-(4,5-diphenyl-2-oxazolyl)-3-biphenylyloxy]acetate
IR (Nujol) : 1600 cm$^{-1}$
NMR (DMSO-d$_6$. δ) : 4.18 (2H, s), 6.84–6.89 (1H, m), 7.15–7.25 (2H, m), 7.32–7.50 (7H, m), 7.62–7.74 (5H, m), 7.80–7.84 (1H, m), 8.08–8.12 (1H, m), 8.29 (1H, m)
(+) APCI Mass : 448 (M$^+$+1)

(18) Sodium [3-[trans-2-hydroxy-2-(4,5-diphenyl-2-oxazolyl)cyclohexyl]phenoxy]acetate
mp : >250° C.
IR (Nujol) : 3350, 1600 cm$^{-1}$
NMR (DMSO-d$_6$, δ) : 1.5–1.7 (5H, br m), 2.14 (3H, br m), 2.85 (1H, br m), 3.97 (2H, s), 5.53 (1H, s), 6.51–6.61 (3H, m), 6.96–6.99 (1H, m), 7.36–7.42 (8H, br m), 7.56–7.60 (2H, br m)
FAB Mass : 492 (M$^+$+1)

(19) Sodium [3-[[trans-2-hydroxy-2-(4,5-diphenyl-2-oxazolyl)cyclohexyl]methyl]phenoxy]acetate
IR (Nujol) : 3350, 1600 cm$^{-1}$
NMR (DMSO-d$_6$, δ) : 1.2–1.6 (7H, br m), 2.04 (1H, br m), 2.24–2.43 (2H, m), 2.79–2.90 (1H, br m), 4.01 (2H, s), 5.77 (1H, br), 6.56–6.62 (3H, m), 7.02–7.10 (1H, m), 7.3–7.7 (10H, m)
(+) APCI Mass : 506 (M$^+$+1)

(20) Sodium [3-[[2-[4,5-bis(4-methylphenyl)-2-oxazolyl]-2-cyclohexen-1-yl]methyl]phenoxy]acetate
mp : 235–250° C.
IR (Nujol) : 1600 cm$^{-1}$
NMR (DMSO-d$_6$, δ) : 1.60 (4H, br), 2.34 (9H, br), 3.09 (2H, m), 4.06 (2H, s), 6.65 (1H, m), 6.77–6.87 (3H, m), 7.09–7.14 (1H, m), 7.25–7.29 (4H, br m), 7.49–7.56 (4H, br m)
FAB Mass : 516 (M$^+$+1)

(21) [3-[[2-[4,5-bis(4-methylphenyl)-2-oxazolyl]-2-cyclopenten-1-yl]methyl]phenoxy]acetic acid
mp : 72.2–80.9° C.
IR (Neat) : 1720, 1600 cm$^{-1}$
NMR (CDCl$_3$, δ) : 1.85 (1H, m), 1.99–2.10 (1H, m), 2.37 (6H, s), 2.43–2.64 (3H, br m), 3.26–3.34 (2H, br m), 4.53 (2H, s), 6.68–6.70 (2H, br m), 6.82–6.90 (2H, br m), 7.13–7.20 (5H, m), 7.45–7.55 (4H, m)
(+) APCI Mass : 480 (M$^+$+1)

(22) Sodium [3-[[cis-2-hydroxy-2-(4,5-diphenyl-2-oxazolyl)-cyclohexyl]methyl]phenoxy]acetate
IR (Nujol) : 3300, 1600 cm$^{-1}$
NMR (DMSO-d$_6$, δ) : 1.24–1.94 (8H, br), 1.94–2.64 (3H, br), 3.43 (1H, s), 4.02 (2H, s), 6.54–6.58 (3H, br), 6.99–7.07 (1H, m), 7.06–7.64 (10H, m)
FAB Mass : 506 (M$^+$+1)

(23) Sodium [3-[[cis-2-methoxy-2-(4,5-diphenyl-2-oxazolyl)cyclohexyl]methyl]phenoxy]acetate
IR (Nujol) : 1605 cm$^{-1}$
NMR (DMSO-d$_6$, δ) : 1.24–1.60 (6H, br m), 1.99–2.29 (3H, br m), 2.37–2.70 (2H, m), 3.34 (3H, s), 4.00 (2H, s), 6.51–6.57 (3H, m), 6.99 (1H, m), 7.33–7.64 (10H, m)
FAB Mass : 520 (M$^+$+1)

(24) Sodium [3-[[2-(4,5-diphenyl-2-oxazolyl)phenyl]methyl]phenoxy]acetate
IR (Nujol) : 1595 cm$^{-1}$
NMR (DMSO-d$_6$, δ) : 3.98 (2H, s), 4.54 (2H, s), 6.58–6.60 (3H, m), 7.04–7.11 (1H, m), 7.39–7.50 (9H, m), 7.58–7.68 (4H, m), 8.09–8.13 (1H, m)
FAB Mass : 484 (M$^+$+1)

(25) (−)-Sodium [3-[[(1R)-2-(4,5-diphenyloxazol-2-yl)-2-cyclopenten-1-yl]methyl]phenoxy]acetate

[α]$_D$: −68.97° (C=0.57, MeOH)

mp :220° C. (dec.)

IR (Nujol) : 1650, 1620, 1590 cm$^{-1}$

NMR (CD$_3$OD, δ) : 1.95–2.07 (2H, m), 2.50–2.67 (3H, m), 3.19–3.28 (1H, m), 3.55 (1H, m), 4.31 (2H, s), 6.69–6.86 (4H, m), 7.07–7.15 (1H, m), 7.35–7.58 (10H, m)

EXAMPLE 27

The following compound was obtained by treating isomer G obtained in Example 16 according to a similar manner to that of Example 2.

Sodium [3-[[cis- or trans-2-[4,5-bis(4-methylphenyl)-2-oxazolyl]cyclohexyl]methyl]phenoxy]acetate (isomer I)

mp : 205.8–220.2° C.

IR (Nujol) : 1610 cm$^{-1}$

NMR (DMSO-d$_6$, δ) : 1.2–2.2 (9H, br m), 2.34 (6H, s), 2.5 (2H, br m), 3.20 (1H, br), 4.03 (2H, s), 6.56–6.60 (3H, br m), 7.02–7.10 (1H, m), 7.20–7.28 (4H, m), 7.41–7.52 (4H, m)

FAB Mass : 518 (M$^+$+1)

EXAMPLE 28

The following compound was obtained by treating isomer H obtained in Example 16 according to a similar manner to that of Example 2.

Sodium [3-[[trans- or cis-2-[4,5-bis(4-methylphenyl)-2-oxazolyl]cyclohexyl]methyl]phenoxy]acetate (isomer J)

isomer J is different from isomer I obtained in Example 27 in configuration.

mp : >250° C.

IR (Nujol) : 1610 cm$^{-1}$

NMR (DMSO-d$_6$, δ) : 1.06–1.30 (2H, br m), 1.61 (4H, br m), 1.72 (2H, br m), 2.33 (6H, s), 2.70 (4H, br m), 4.03 (2H, s), 6.56–6.59 (3H, br m), 7.00–7.09 (1H, m), 7.19–7.27 (4H, m), 7.40–7.50 (4H, m)

FAB Mass : 518 (M$^+$+1)

We claim:

1. A compound of the formula:

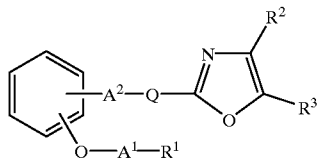

wherein R$^1$ is carboxy or protected carboxy;
R$^2$ is aryl, which is optionally substituted;
R$^3$ is aryl, which is optionally substituted;
A$^1$ is lower alkylene;
A$^2$ is a direct bond or lower alkylene; and
-Q- is a group of the formula:

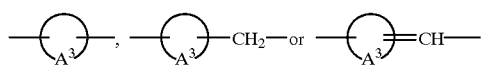

wherein the group:

is cyclo(lower)alkane, or cyclo(lower)alkene, each of which is optionally substituted, or a pharmaceutically acceptable salt thereof.

2. The compound of claim 1, wherein R$^2$ or R$^3$ or both have 1 to 3 substituents.

3. The compound of claim 2, wherein said cyclo(lower)alkane or said cyclo(lower alkene or both contain from 1 to 3 substituents.

4. The compound of claim 1, wherein R$^2$ is phenyl or lower alkylphenyl, and R$^3$ is phenyl or lower alkylphenyl.

5. The compound of claim 4, wherein said substituents for said cyclo(lower)alkane and said cyclo(lower)alkene are selected from the group consisting of epoxy, hydroxy and lower alkoxy.

6. The compound of claim 5, wherein A$^1$ is C$_1$–C$_3$ alkylene, and A$^2$ is a direct bond or C$_1$–C$_3$ alkylene.

7. The compound of claim 6, wherein R$^1$ is carboxy or lower alkoxycarbonyl, A$^1$ is methylene, and A$^2$ is a direct bond or methylene.

8. The compound of claim 7,
wherein R$^1$ is carboxy;
R$^2$ is phenyl or lower alkylphenyl;
R$^3$ is phenyl or lower alkylphenyl;
A$^1$ is methylene;
A$^2$ is methylene; and
-Q- is selected from the group consisting of

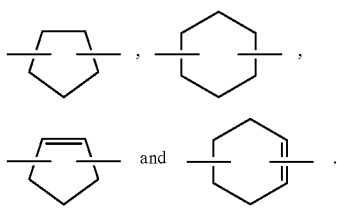

9. The compound of claim 8, which is selected from the group consisting of sodium [3[[(1S)-2-(4,5-diphenyloxazol-2-yl)2-cyclopenten-1-yl]methyl]phenoxy] acetate, sodium [3-[[(1S)-2-(4,5-diphenyloxazol-2-yl)-2-cyclohexen-1-yl]methyl]phenoxy] acetate, sodium [3-[[2-(4,5-diphenyloxazol-2-yl)-cyclopentyl]methyl]phenoxy]acetate, and sodium [3-[[2-(4,5-bis)4-methylphenyl)oxazol-2-yl)cyclohexyl]methyl]phenoxy]acetate.

10. A process for preparing a compound of the formula:

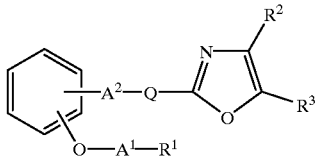

wherein R$^1$ is carboxy or protected carboxy;
R$^2$ is aryl, which is optionally substituted;
R$^3$ is aryl which is optionally substituted;
A$^1$ is lower alkylene;
A$^2$ is a direct bond or lower alkylene; and -Q- is a group of the formula:

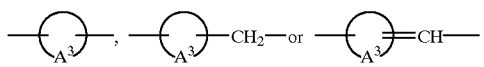

wherein the group:

is cyclo(lower)alkane or cyclo(lower)alkene, each of which is optionally substituted, or a salt thereof, which process comprises:

reacting a compound of the formula:

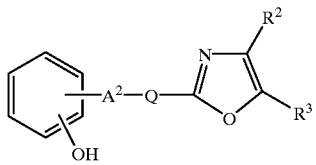

wherein $R^2$, $R^3$, $A^2$ and -Q- are each as defined above, or a salt thereof, with a compound of the formula:

wherein $R^1$ and $A^1$ are each as defined above; and $X^1$ is an acid residue,
or a salt thereof, to yield a compound of the formula:

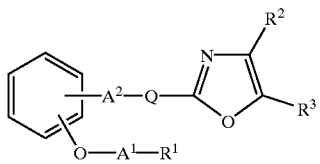

wherein $R^1$, $R^2$, $R^3$, $A^1$, $A^2$ and -Q- are each as defined above;

or a salt thereof.

11. A pharmaceutical composition, which comprises, as an active ingredient, an effective amount of one or more compounds of claim 1, or a pharmaceutically acceptable salt thereof in admixture with a pharmaceutically acceptable carrier.

12. A method for treating or preventing arterial obstruction, restenosis after percutaneous transluminal coronary angioplasty, arteriosclerosis, cerebrovascular disease or ischemic heat disease, which comprises administering one or more compounds of claim 1 or a pharmaceutically acceptable salt thereof to a mammal in need thereof.

13. The method of claim 12, wherein said mammal is human.

14. A method for effecting prostaglandin 2 agonist activity, which comprises administering an effective amount of one or more of the compounds of claim 1 or a pharmaceutically acceptable salt thereof to a mammal in need thereof.

15. The method of claim 14, wherein said mammal is human.

16. A method for inhibiting platelet aggregation, which comprises administering an effective amount of one or more of the compounds of claim 1 or a pharmaceutically acceptable salt thereof to a mammal in need thereof.

17. The method of claim 16, wherein said mammal is human.

18. A method of suppressing blood pressure, which comprises administering an effective amount of one or more of the compounds or a pharmaceutically acceptable salt thereof of claim 1, to a mammal in need thereof.

19. The method of claim 18, wherein said mammal is human.

* * * * *